(12) United States Patent
Hoffman et al.

(10) Patent No.: US 8,155,479 B2
(45) Date of Patent: Apr. 10, 2012

(54) AUTOMATED PANNING AND DIGITAL ZOOMING FOR ROBOTIC SURGICAL SYSTEMS

(75) Inventors: Brian D. Hoffman, Sunnyvale, CA (US); Christopher J. Hasser, Los Altos, CA (US); William C. Nowlin, Los Altos, CA (US)

(73) Assignee: Intuitive Surgical Operations Inc., Sunnyvale, CA (US)

( * ) Notice: Subject to any disclaimer, the term of this patent is extended or adjusted under 35 U.S.C. 154(b) by 1048 days.

(21) Appl. No.: 12/058,663

(22) Filed: Mar. 28, 2008

(65) Prior Publication Data

US 2009/0245600 A1 Oct. 1, 2009

(51) Int. Cl.
*G06K 9/36* (2006.01)
(52) U.S. Cl. ............... 382/276; 348/240.99; 348/246
(58) Field of Classification Search .................. None
See application file for complete search history.

(56) References Cited

U.S. PATENT DOCUMENTS

| | | |
|---|---|---|
| 4,179,823 A | 12/1979 | Sullivan et al. |
| 5,247,612 A | 9/1993 | Quinard |
| 5,765,045 A | 6/1998 | Takagi et al. |
| 5,831,667 A | 11/1998 | Siminou |
| 5,861,940 A | 1/1999 | Robinson et al. |
| 5,912,721 A | 6/1999 | Yamaguchi et al. |
| 6,451,027 B1 | 9/2002 | Cooper et al. |
| 6,456,262 B1 | 9/2002 | Bell |
| 6,522,906 B1 | 2/2003 | Salisbury, Jr. et al. |
| 6,529,331 B2 | 3/2003 | Massof et al. |
| 6,578,962 B1 | 6/2003 | Amir et al. |
| 6,779,065 B2 | 8/2004 | Murty et al. |
| 6,995,774 B2 | 2/2006 | Tognoni et al. |
| 7,965,425 B2 * | 6/2011 | Silverbrook ................. 358/498 |
| 2007/0257996 A1 * | 11/2007 | Kurosawa et al. ....... 348/240.99 |

OTHER PUBLICATIONS

Ames, Ben, "Streamlined databases drive military simulation," Military and Aerospace Electronics Magazine, Nov. 2005, vol. 16, Issue 11, 10 pages: Internet: http://mae.pennnet.com/display_article/241260/32/ARTCL/none/none/1/Streamlined-databases-drive-military-simulation/.

Bediz, Yusuf and Gozde Bozdagi Akar, "View point tracking for 3D display systems," 13th European Signal Processing Conference (EUSIPCO 2005), Sep. 2005, Turkey, 4 pages, Internet: http://www.eurasip.org/Proceedings/Eusipco/Eusipco2005/defevent/papers/cr1328.pdf.

Beymer, David and Myron Flickner, "Eye Gaze Tracking Using an Active Stereo Head," Proceedings of 2003 IEEE Computer Society Conference on Computer Vision and Pattern Recognition (CVPR '03), Jun. 18-20, 2003, vol. 2, 8 pages.

(Continued)

*Primary Examiner* — Jermele M Hollington
*Assistant Examiner* — Trung Nguyen

(57) ABSTRACT

In one embodiment of the invention, a digital zoom and panning system for digital video is disclosed including an image acquisition device to capture digital video images; an image buffer to store one or more frames of digital video images as source pixels; a display device having first pixels to display images; a user interface to accept user input including a source rectangle to select source pixels within frames of the digital video images, a destination rectangle to select target pixels within the display device to display images, and a region of interest within the digital video images to display in the destination rectangle; and a digital mapping and filtering device to selectively map and filter source pixels in the region of interest from the image buffer into target pixels of the display device in response to the user input.

27 Claims, 19 Drawing Sheets

OTHER PUBLICATIONS

Brainlab, BrainSUITE Net product page, 2007, 1 page; Internet: http://www.brainlab.com/scripts/website_english.asp?articleID=2258andarticleTypeID=261andpageTypeID=4.

Brainlab, VectorVision product page, 2007, 1 page; Internet: http://www.brainlab.com/scripts/website_english.asp?articleID=2275andarticleTypeID=261andpageTypeID=4.

Darrell, Trevor et al., "Exploring Vision-Based Interfaces: How to Use Your Head in Dual Pointing Tasks," MIT Artificial Intelligence Laboratory AI Memo 2002-001, Jan. 2002, 9 pages, Internet: http://people.csail.mit.edu/aoh/papers/ai_memo.pdf.

Dugdale, Jon et al., "Current Developments in Visual Display Technology for Fighter Type Simulators," as posted online Oct. 18, 2006, 11 pages; Internet: http://www.link.com/pdfs/itsec.pdf.

Heidrich, Wolfgang et al., "Applications of Pixel Textures in Visualization and Realistic Image Synthesis," ACM Symposium on Interactive 3D Graphics, Atlanta, Georgia, USA, Apr. 26-29, 1999, pp. 127-134.

Jesme, Ronald D., "Low Vision Enhancement System," 1995 Virtual Reality Conference, 4 pages, 1995; Internet: http://www.csun.edu/cod/conf/1995/proceedings/0021.htm.

Mylonas, George P. et al., "Gaze-contingent control for minimally invasive robotic Surgery," Computer Aided Surgery, vol. 11, Issue 5, pp. 256-266, Sep. 2006.

Mylonas, George P. et al., "Gaze-contingent Depth Recovery and Motion Stabilisation for Minimally Invasive Robotic Surgery," Medical Imaging and Augmented Reality (MAIR-2004), Lecture Notes in Computer Science, vol. 3150/2004, pp. 311-319, Springer-Verlag, 2004.

SGI, News article: "SGI to Provide High-Performance Visual Systems for US Army AVCATT-A," Apr. 24, 2000, 2 pages; Internet: http://www.thefreelibrary.com/SGI+TO+PROVIDE+HIGH-PERFORMANCE+VISUAL+SYSTEMS+FOR+US+ARMY+AVCATT-A-a061693863.

Sisodia, Ashok et al., "Advanced Helmet Mounted Display (AHMD)," 2007, 11 Pages; Internet: http://www.link.com/pdfs/AHMD_2007_Paper.pdf.

Starner, Thad et al., "Wearable Computing and Augmented Reality," M.I.T. Media Lab Vision and Modeling Group Technical Report No. 355, Nov. 1995, 19 pages.

Talmi, K. and J. Liu, "Eye and Gaze Tracking for Visually Controlled Interactive Stereoscopic Displays," Signal Processing: Image Communication, vol. 14, pp. 799-810, 1999.

Turkowski, Ken, "Filters for Common Resampling Tasks," Apr. 10, 1990, 14 pages, Internet: http://www.worldserver.com/turk/computergraphics/ResamplingFilters.pdf.

Venkatachalam, Rajashekar et al., "Digital Zoom for Low Vision Enhancement Systems," 10 pages, 2004; Internet: http://www.cse.yorku.ca/visor/pdf/EI2004_digital_zoom.pdf.

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

Wikipedia, entry on "Pixel," printed Dec. 20, 2007 at 1:18 p.m. 5 pages.

Wikipedia, entry on "Texel," printed Dec. 20, 2007 at 1:10 p.m., 1 page.

Wikipedia, entry on "Texture mapping," printed Dec. 20, 2007 at 1:11 p.m., 3 pages.

Yang, Guang-Zhong et al., "Visual search: psychophysical models and practical applications," Image and Vision Computing, Elsevier, vol. 20, pp. 291-305, 2002.

* cited by examiner

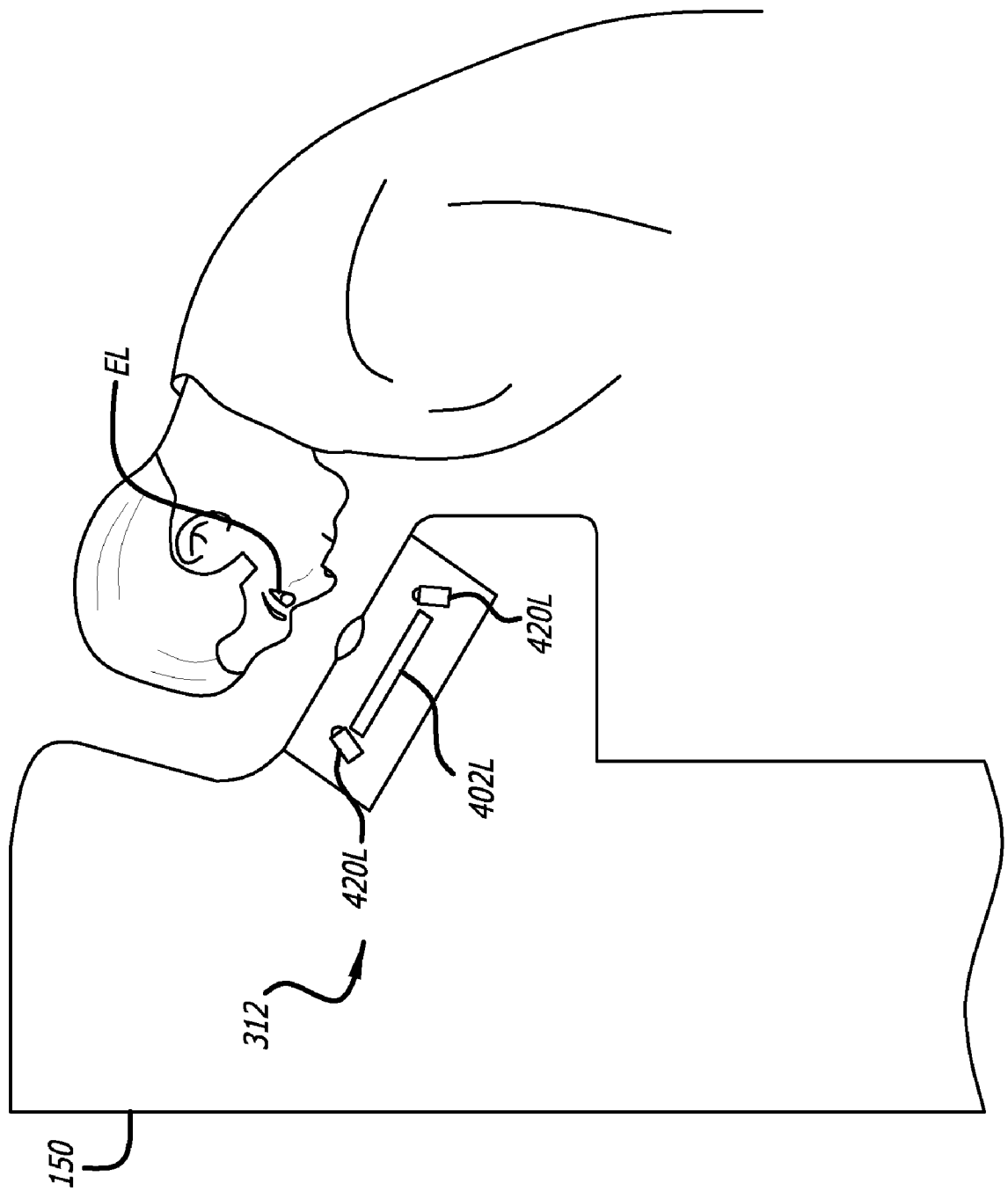

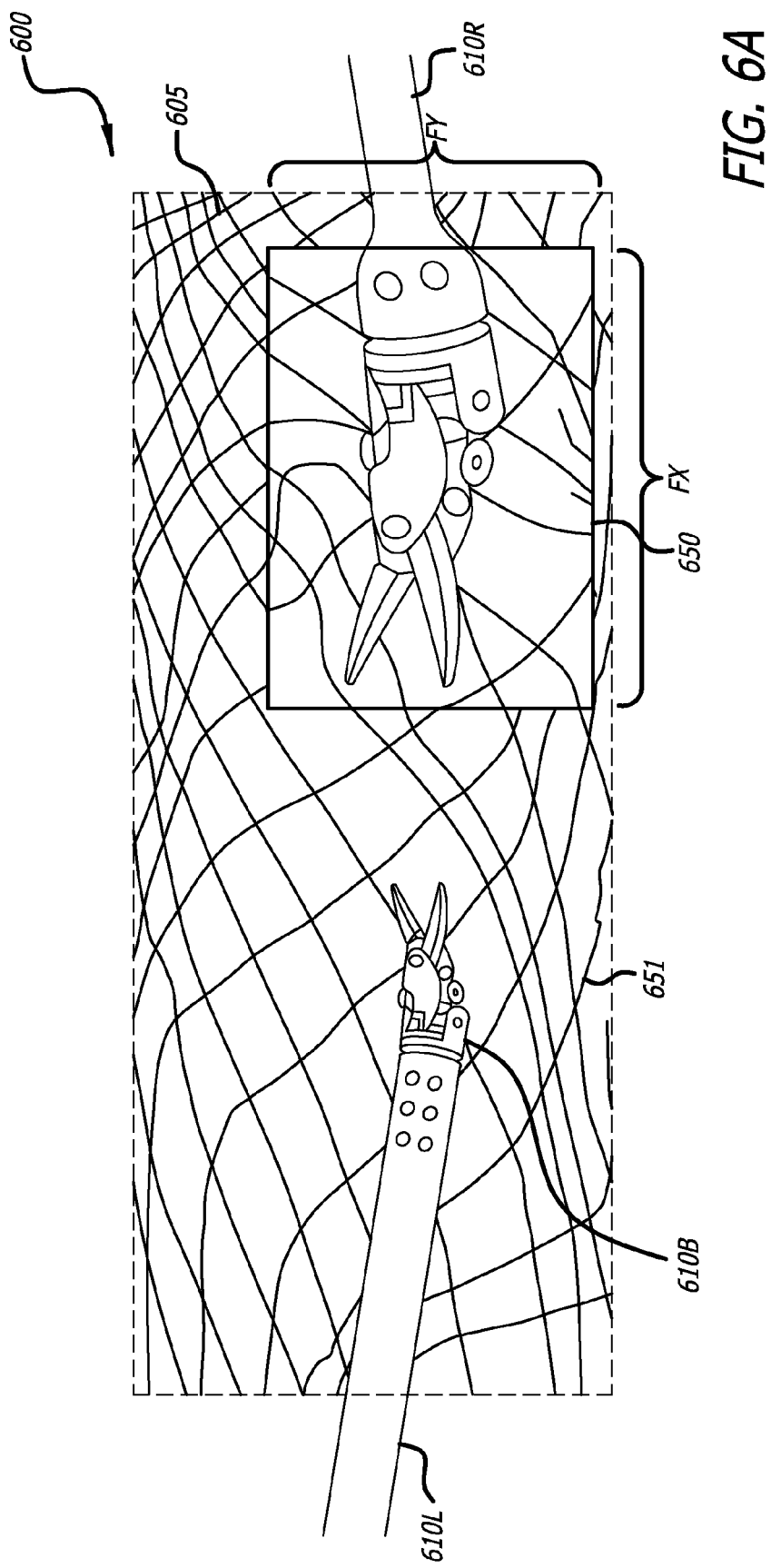

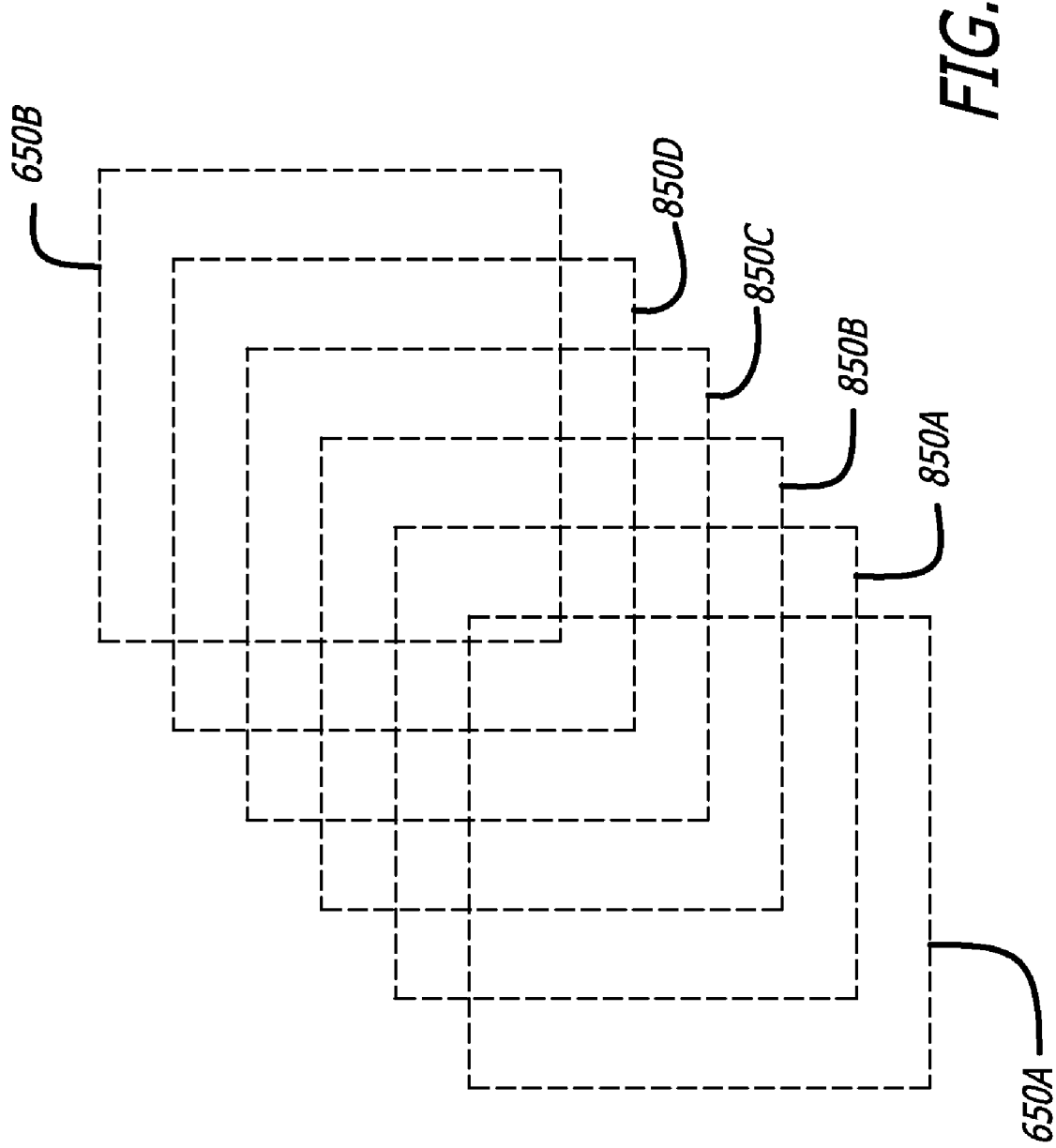

AUTOMATED PANNING AND DIGITAL ZOOMING FOR ROBOTIC SURGICAL SYSTEMS

FIELD

The embodiments of the invention relate generally to vision subsystems for minimally invasive robotic surgical systems.

BACKGROUND

Minimally invasive surgical (MIS) procedures have become more common using robotic (e.g., telerobotic) surgical systems. An endoscopic camera is typically used to provide images to a surgeon of the surgical cavity so that the surgeon can manipulate robotic surgical tools therein.

A surgeon's focus is typically on the tissue or organs of interest in a surgical cavity. He may manually move the endoscopic camera in and around a surgical site or cavity to properly see and manipulate tissue with robotic surgical tools. However, when the endoscopic camera is manually moved inward so that tissue is at desired magnifications, typically a narrow field of view is provided of the surgical cavity by the endoscopic camera. Tools or tissue that are outside the field of view typically require the surgeon to manually cause the endoscopic camera to move to a different position or manually move the camera back out.

Some times the endoscopic camera is slightly moved left, right, up, and/or down to see a slightly different view or slightly moved out to obtain a slightly larger field of view and then moved right back to the original position to the desired magnification to manipulate tissue.

Some times a surgeon may have to initially guess which direction to move the endoscopic camera to position the tissue and/or tool of interest in the surgical cavity within the field view of the endoscopic camera.

A more efficient use of the endoscopic camera may also make surgical procedures with a robotic surgical system more efficient.

BREIF SUMMARY

The embodiments of the invention are summarized by the claims that follow below.

BRIEF DESCRIPTIONS OF THE DRAWINGS

FIG. 4A is a cutaway side view of the stereo viewer with gaze detection in the robotic surgical master control console.

FIG. 6A is a perspective view of a video frame including video images of a surgical site with a digital zoomed fovea portion.

FIG. 8 illustrates a gradual movement of the digital zoom portion over multiple frames of video information.

DETAILED DESCRIPTION

Figure 1A:
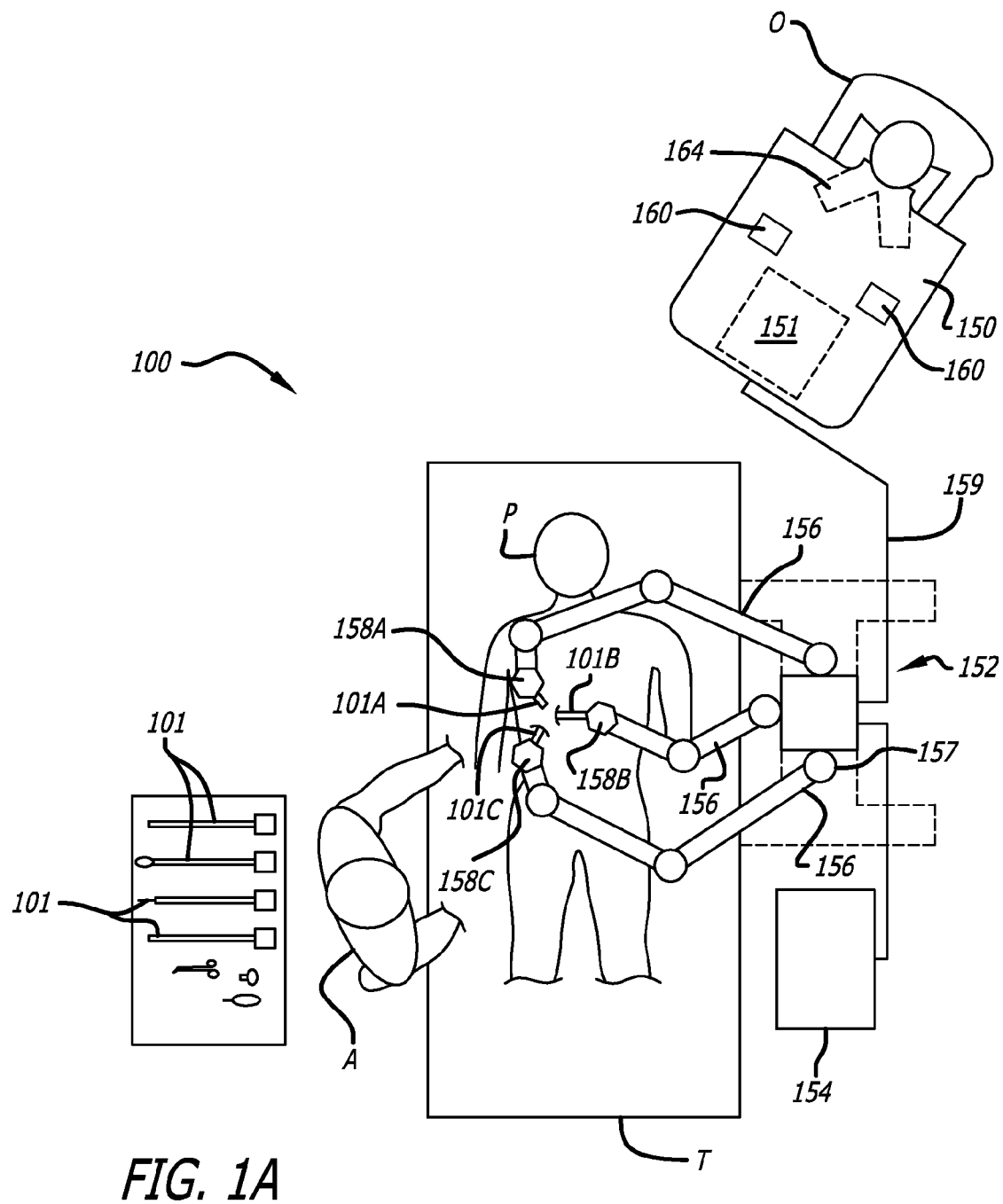
FIG. 1A is a block diagram of a robotic medical system including a stereo viewer and an image guided surgery (IGS) system with a tool tracking sub-system.

In the following detailed description of the embodiments of the invention, numerous specific details are set forth in order to provide a thorough understanding of the present invention.

However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

Introduction

Aspects of the invention include methods, apparatus and systems for automated panning and digital zooming for video subsystems of robotic surgical systems.

High definition endoscopic cameras may generate a greater number of pixels than can be displayed by liquid crystal display panels or display monitors. Aspects of some of the disclosed embodiments of the invention may use some of the extra pixel information captured by high definition endoscopic cameras that would otherwise be unused and possibly discarded.

Automatic camera following, an aspect of some embodiments of the invention, is disclosed that may be responsive to robotic surgical instrument location using API information, or selection of an active area in a surgical site into which the surgeon desires to gaze.

A linear digital zoom, another aspect of some embodiments of the invention, is disclosed that linearly scales a spatial subset of a source of high definition video images on one or more displays. The full spatial high definition video images may be linearly scaled down or down-sampled and displayed picture-in-picture (PIP) as a navigation window or a pull-back view for example.

On the same display device, a linear digital zoom of a spatial subset of the source the high definition video images may combined with a non-linear digital zoom of another spatial subset of the source of the high definition video images, in some embodiments of the invention. A first spatial subset of the source of the high definition video images may be digitally zoomed linearly and displayed or rendered in a target window portion (fovea) on a display device and concurrently a second spatial subset of the source of the high definition video images around the first spatial subset may be digitally zoomed non-linearly and displayed or rendered in a target frame portion (background or surround) around the target window portion (fovea) on the display device to provide a smooth image transition.

The frame portion (background or surround) with the second spatial subset of the source of the high definition video images altered by a non-linear digital zoom factor may be used to complete the surgeon's field of view around the window portion (fovea). In one configuration of the invention, the target window portion (fovea) may be displayed in high-resolution while the frame portion (background or surround) is displayed with a lower-resolution to provide an improved sense of peripheral vision. With an improved sense of peripheral vision, the need for a PIP navigation window of the surgical site displayed on the display monitor is reduced. The frame portion (background or surround) with the non-linear digital zoom may reduce the number of otherwise frequent short duration camera control events. Short duration camera control events are adjustments in the endoscopic camera that are often made due to a surgeon's desire to see what is just-outside-the-field-of-view or in reaction to lack of peripheral vision, rather than adjustments made to obtain a better field of view of the operative site.

Automatic camera following may be combined together with a digital zoom in some embodiments of the invention such that the digital zoomed portion of an image tracks or follow a surgeon's motions, such as the gaze of his pupils, without requiring mechanical movement of the endoscopic camera. If the surgeon's motions indicate that the digital zoomed portion extend beyond pixels of the high definition digital image being captured, the endoscopic camera may be mechanically moved or panned automatically.

For automatic camera following, different sensing modalities may be used to detect a surgeon's motion so that a digital zoomed portion of interest of an image may be moved around within the pixels of a high definition digital image. Some different sensing modalities include (1) robotic surgical tool tracking, (2) surgeon gaze tracking; (3) or a discrete user interface. Robotic surgical tool tracking may be performed by kinematics sensing through joint encoders, potentiometers, and the like; video analysis-based tool location tracking; or a combination or fusion of kinematics sensing and video analysis-based tool location tracking. A discrete user interface may include one or more of button actuation (such as arrow buttons to the side of a surgeon's console), button presses of master console handle buttons, foot-pedal presses, or voice recognition activation. The discrete user interface may be used to re-center the digital zoomed image based on current tool position, gaze location, or the like. Alternatively, the discrete user interface may be used to re-center or move the image at discrete times, such as through voice activation, perhaps in concert with tool tracking or gaze detection.

Robotic Medical System

Referring now to FIG. 1A, a block diagram of a robotic surgery system 100 is illustrated to perform minimally invasive robotic surgical procedures on a patient P on an operating table T using one or more robotic arms 158A-158C (collectively referred to as robotic arms 158). The one or more robotic arms often support a robotic instrument 101. For instance, a robotic surgical arm (e.g., the center robotic surgical arm 158B) may be used to support a stereo or three-dimensional surgical image capture device (endoscopic camera) 101B such as a stereo endoscope (which may be any of a variety of structures such as a stereo laparoscope, arthroscope, hysteroscope, or the like), or, optionally, some other imaging modality (such as ultrasound, fluoroscopy, magnetic resonance imaging, or the like).

Robotic surgery may be used to perform a wide variety of surgical procedures, including but not limited to open surgery, neurosurgical procedures (e.g., stereotaxy), endoscopic procedures (e.g., laparoscopy, arthroscopy, thoracoscopy), and the like.

A user or operator O (generally a surgeon) performs a minimally invasive surgical procedure on patient P by manipulating control input devices (touch sensitive master control handles) 160 at a master control console 150. A computer 151 of the console 150 directs movement of robotically controlled endoscopic surgical instruments (robotic surgical tools or robotic instruments) 101A-101C via control lines 159, effecting movement of the instruments using a robotic patient-side system 152 (also referred to as a patient-side cart). In a stereo display device 164 of the master control console 150, the operator O views video images of the surgical site including the robotic surgical tools that are in the field of view of the endoscopic camera 101B.

The robotic patient-side system 152 includes one or more robotic arms 158. Typically, the robotic patient-side system 152 includes at least three robotic surgical arms 158A-158C (generally referred to as robotic surgical arms 158) supported by corresponding positioning set-up arms 156. The central robotic surgical arm 158B may support an endoscopic camera 101B. The robotic surgical arms 158A and 158C to the left and right of center may support robotic instruments 101A and 101C, respectively, that may manipulate tissue.

Robotic instruments (robotic surgical tools) are generally referred to herein by the reference number 101. Robotic instruments 101 may be any instrument or tool that couples to a robotic arm that can be manipulated thereby and can report back kinematics information to the robotic system. Robotic instruments include, but are not limited to, surgical tools, medical tools, bio-medical tools, and diagnostic instruments (ultrasound, computer tomography (CT) scanner, magnetic resonance imager (MRI)).

Generally, the robotic patient-side system 152 includes a positioning portion and a driven portion. The positioning portion of the robotic patient-side system 152 remains in a fixed configuration during surgery while manipulating tissue. The driven portion of the robotic patient-side system 152 is actively articulated under the direction of the operator O generating control signals at the surgeon's console 150 during surgery. The driven portion of the robotic patient-side system 152 may include, but is not limited or restricted to robotic surgical arms 158A-158C.

The instruments 101, the robotic surgical arms 158A-158C, and the set up joints 156,157 may include one or more displacement transducers, positional sensors, and/or orientational sensors 185,186 to assist in acquisition and tracking of robotic instruments. From instrument tip to ground (or world coordinate) of the robotic system, the kinematics information generated by the transducers and the sensors in the robotic patient-side system 152 may be reported back to a tracking system 352 of the robotic surgical system.

As an exemplary embodiment, the positioning portion of the robotic patient-side system 152 that is in a fixed configuration during surgery may include, but is not limited or restricted to set-up arms 156. Each set-up arm 156 may include a plurality of links and a plurality of joints. Each set-up arm may mount via a first set-up-joint 157 to the patient side system 152.

An assistant A may assist in pre-positioning of the robotic patient-side system 152 relative to patient P as well as swapping tools or instruments 101 for alternative tool structures, and the like, while viewing the internal surgical site via an external display 154. The external display 154 or some other external display may be positioned or located elsewhere so that images of the surgical site may be displayed to students or other interested persons during a surgery. Images with additional information may be overlaid onto the images of the surgical site by the robotic surgical system for display on the external display 154.

Figure 1B:
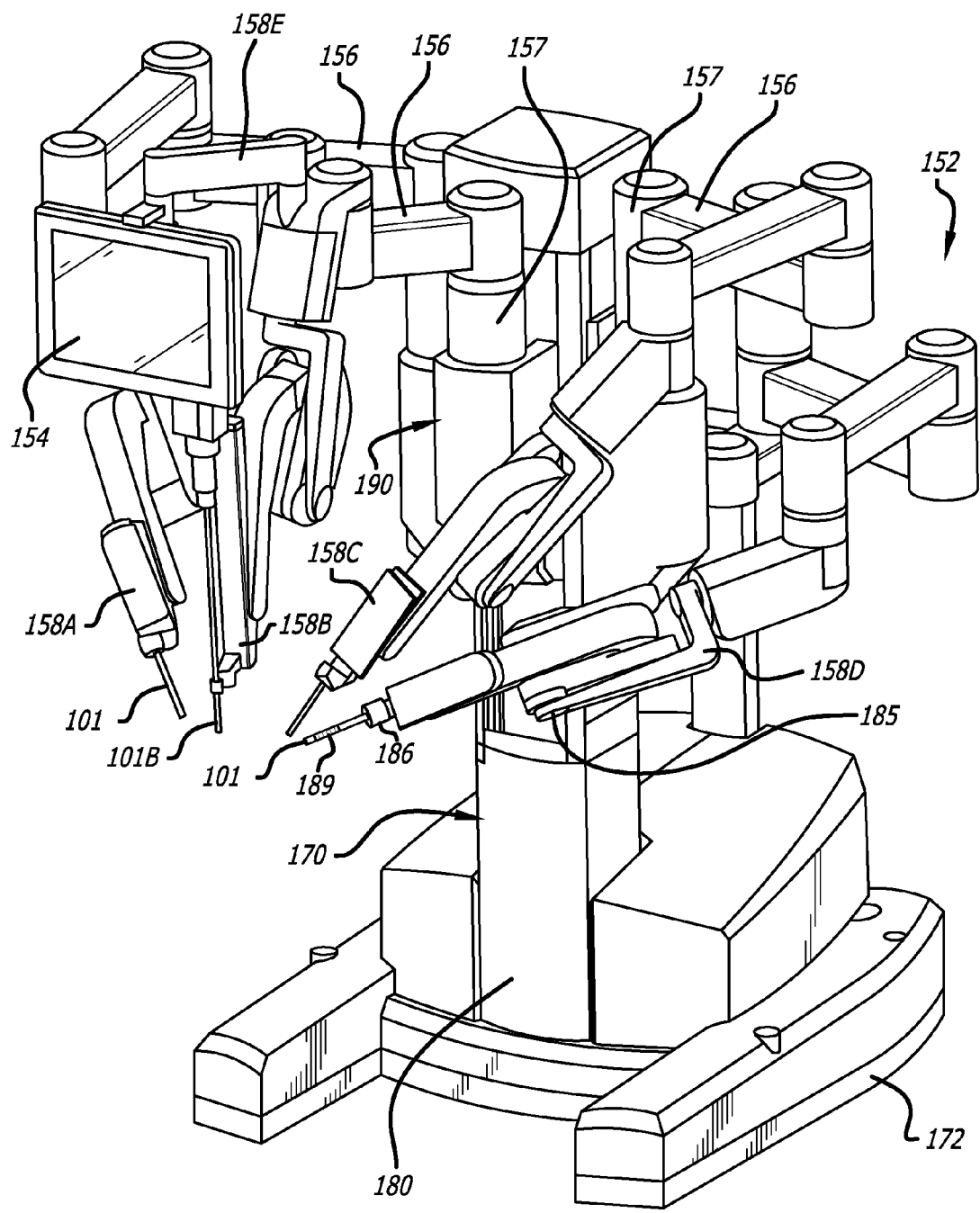
FIG. 1B is a block diagram of a patient side cart including robotic surgical arms to support and move robotic instruments.

Referring now to FIG. 1B, a perspective view of the robotic patient-side system 152 is illustrated. The robotic patient-side system 152 comprises a cart column 170 supported by a base 172. One or more robotic surgical arms 158 are respectively attached to one or more set-up arms 156 that are a part of the positioning portion of robotic patient-side system 152. Situated approximately at a central location on base 172, the cart column 170 includes a protective cover 180 that protects components of a counterbalance subsystem and a braking subsystem (described below) from contaminants.

Excluding a monitor arm 158E for the monitor 154, each robotic surgical arm 158 is used to control robotic instruments 101A-101C. Moreover, each robotic surgical arm 158 is coupled to a set-up arm 156 that is in turn coupled to a carriage housing 190 in one embodiment of the invention, as described below with reference to FIG. 3. The one or more robotic surgical arms 158 are each supported by their respective set-up arm 156, as is illustrated in FIG. 1B.

The robotic surgical arms 158A-158D may each include one or more displacement transducers, orientational sensors, and/or positional sensors 185 to generate raw uncorrected kinematics data, kinematics datum, and/or kinematics information to assist in acquisition and tracking of robotic instruments. The robotic instruments may also include a displacement transducer, a positional sensor, and/or orientation sensor 186 in some embodiments of the invention. Moreover, one or more robotic instruments may include a marker 189 to assist in acquisition and tracking of robotic instruments.

Robotic Surgical Arms

Figure 1C:
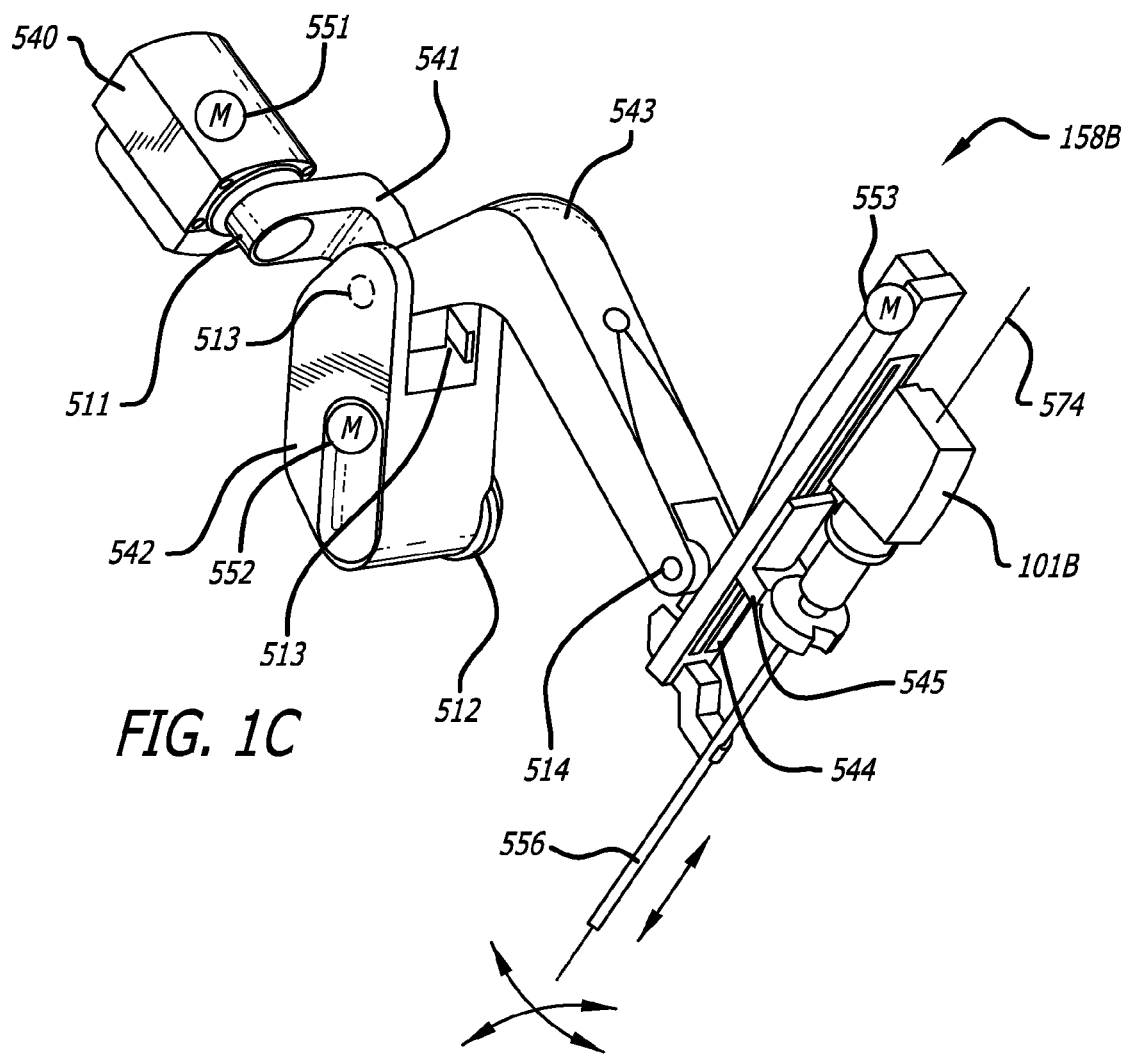
FIG. 1C is perspective view of an endoscopic camera manipulator or robotic surgical arm.

Referring now to FIG. 1C, a perspective view of the robotic surgical arm 158B is illustrated. As discussed previously, the center robotic surgical arm 158B is for coupling to an endoscopic camera 101B. The endoscopic camera 101B may not have an end effector that requires controlling. Thus, fewer motors, cables, and pulleys may be employed in controlling the endoscopic camera 101B. However for the purposes of overall movement (e.g., pitch, yaw, and insertion), the elements of the center robotic surgical arm 158B are similar to the elements of the robotic surgical arms 158A,158C.

In robotic surgical systems for minimally invasive surgery, it is desirable to move and constrain a robotic surgical tool at a single fixed remote center point 556. Typically the fixed remote center point 556 is near the point of insertion of the surgical tool into the patient P. The center of rotation 556 may be aligned with the incision point to the internal surgical site, for example, by a trocar or cannula at an abdominal wall during laparoscopic surgery. As the fixed remote center point 556 is on the insertion axis 574 of the robotic camera and is offset and remote from ground, the robotic surgical arm may also be referred as an offset remote center manipulator instead.

The robotic surgical arm 158B includes serial links 541-545 pivotally coupled in series at joints 512-514 near respective ends of the links. The first link (Link 1) 541 is pivotally coupled to a drive mount 540 at a first joint 511 near a first end and the second link (Link 2) 542 at the second joint 512 near a second end. The third link (Link 3) 543 is pivotally coupled to the second link 542 near a first end and pivotally coupled to the fourth link (Link 4) 544 near a second end. Generally, the fourth link 544 is substantially in parallel to the insertion axis 574 of the endoscopic camera 101B. A fifth link (Link 5) 545 is slidingly coupled to the fourth link 544. The endoscopic camera 101B mounts to the fifth link 545 as shown.

The robotic surgical arm 158B further includes a mounting base 540 that allows it to be mounted and supported by set-up arms/joints of a patient side system. The mounting base 540 is pivotally coupled to the first link 541 and includes a first motor 551 to yaw the robotic surgical arm about a yaw axis at the pivot point. The second link 542 houses a second motor 552 to drive and pitch the linkage of the arm about a pitch axis at the pivot point 556. The fourth link 544 may include a third motor 553 to slide the firth link 545 and the endoscopic camera 101B along the insertion axis 574.

The robotic endoscopic camera arm 158B and the robotic surgical arms 158A,158C have a drive train system driven by the motors 551-553 to control the pivoting of the links about the joints 512-514. If the endoscopic camera 101B is to be mechanically moved, one or more of the motors 551-553 coupled to the drive train are energized to move the links of the robotic endoscopic camera arm 158B. Other tools 101 attached to the robotic surgical arms 158A,158C may be similarly moved.

Endoscopic Video System

Figure 2:
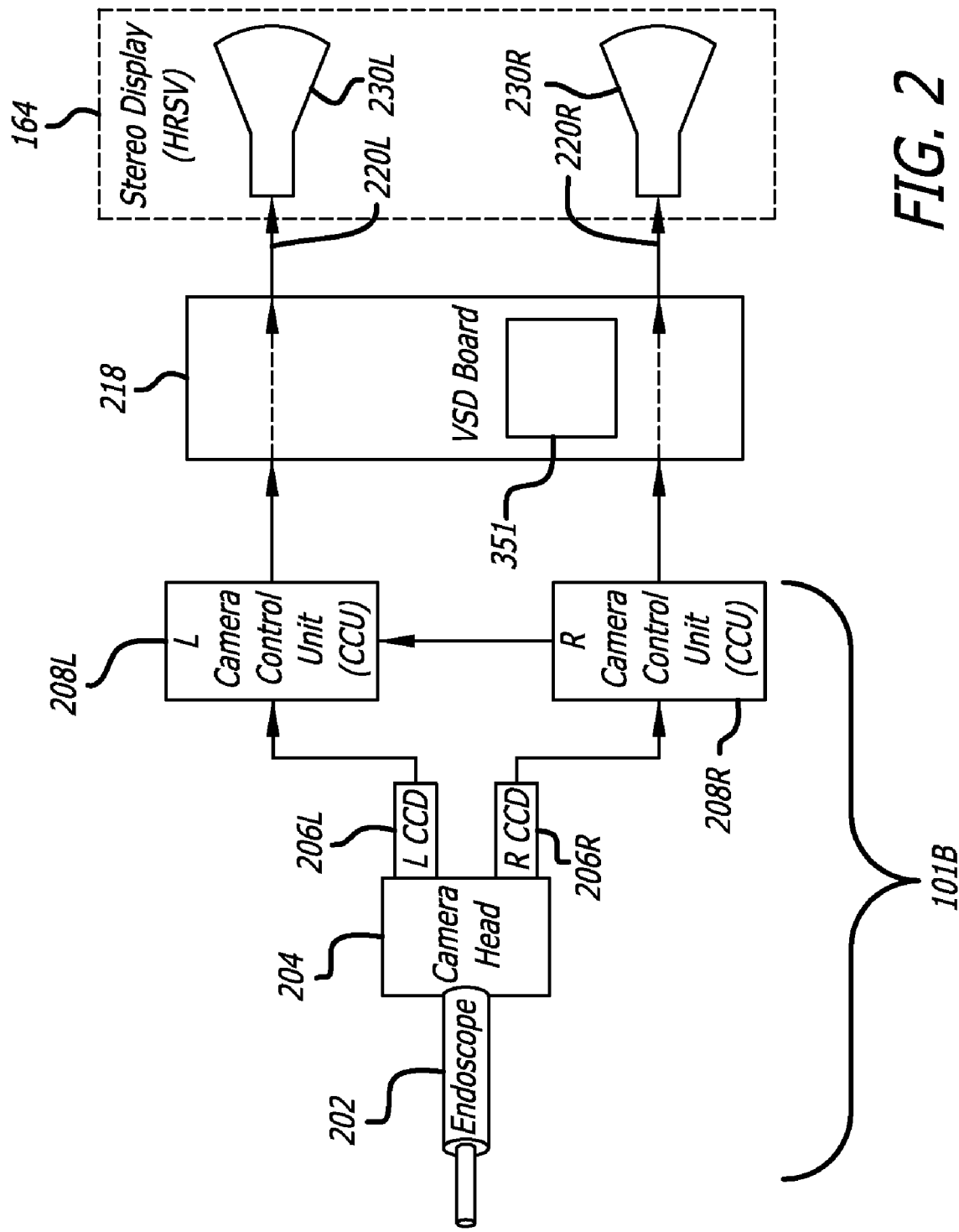
FIG. 2 is a functional block diagram of the video portion of the IGS system to provide a stereo image in both left and right video channels to provide three-dimensional images in a stereo viewer.

Referring now to FIG. 2, the stereo endoscopic camera 101B includes an endoscope 202 for insertion into a patient, a camera head 204, a left image forming device (e.g., a charge coupled device (CCD)) 206L, a right image forming device 206R, a left camera control unit (CCU) 208L, and a right camera control unit (CCU) 208R coupled together as shown. The stereo endoscopic camera 101B generates a left video channel 220L and a right video channel 220R of frames of images of the surgical site coupled to a stereo display device 164 through a video board 218. To initially synchronize left and right frames of data, a lock reference signal is coupled between the left and right camera control units 208L,208R. The right camera control unit generates the lock signal that is coupled to the left camera control unit to synchronize the left view channel to the right video channel. However, the left camera control unit 208L may also generate the lock reference signal so that the right video channel synchronizes to the left video channel.

The stereo display device 164 includes a left monitor 230L and a right monitor 230R. As discussed further herein, the viewfinders or monitors 230L,230R may be provided by a left display device 402L and a right display device 402R, respectively. The stereo images may be provided in color by a pair of color display devices 402L,402R.

Additional details of a stereo endoscopic camera and a stereo display may be found in U.S. Pat. No. 5,577,991 entitled "Three Dimensional Vision Endoscope with Position Adjustment Means for Imaging Device and Visual Field Mask" filed on Jul. 7, 1995 by Akui et al; U.S. Pat. No. 6,139,490 entitled "Stereoscopic Endoscope with Virtual Reality Viewing" filed on Nov. 10, 1997 by Breidenthal et al; and U.S. Pat. No. 6,720,988 entitled "Stereo Imaging System and Method for use in Telerobotic Systems" filed on Aug. 20, 1999 by Gere et al.; all of which are incorporated herein by reference. Stereo images of a surgical site may be captured by other types of endoscopic devices and cameras with different structures. For example, a single optical channel may be used with a pair of spatially offset sensors to capture stereo images of the surgical site.

Figure 3:
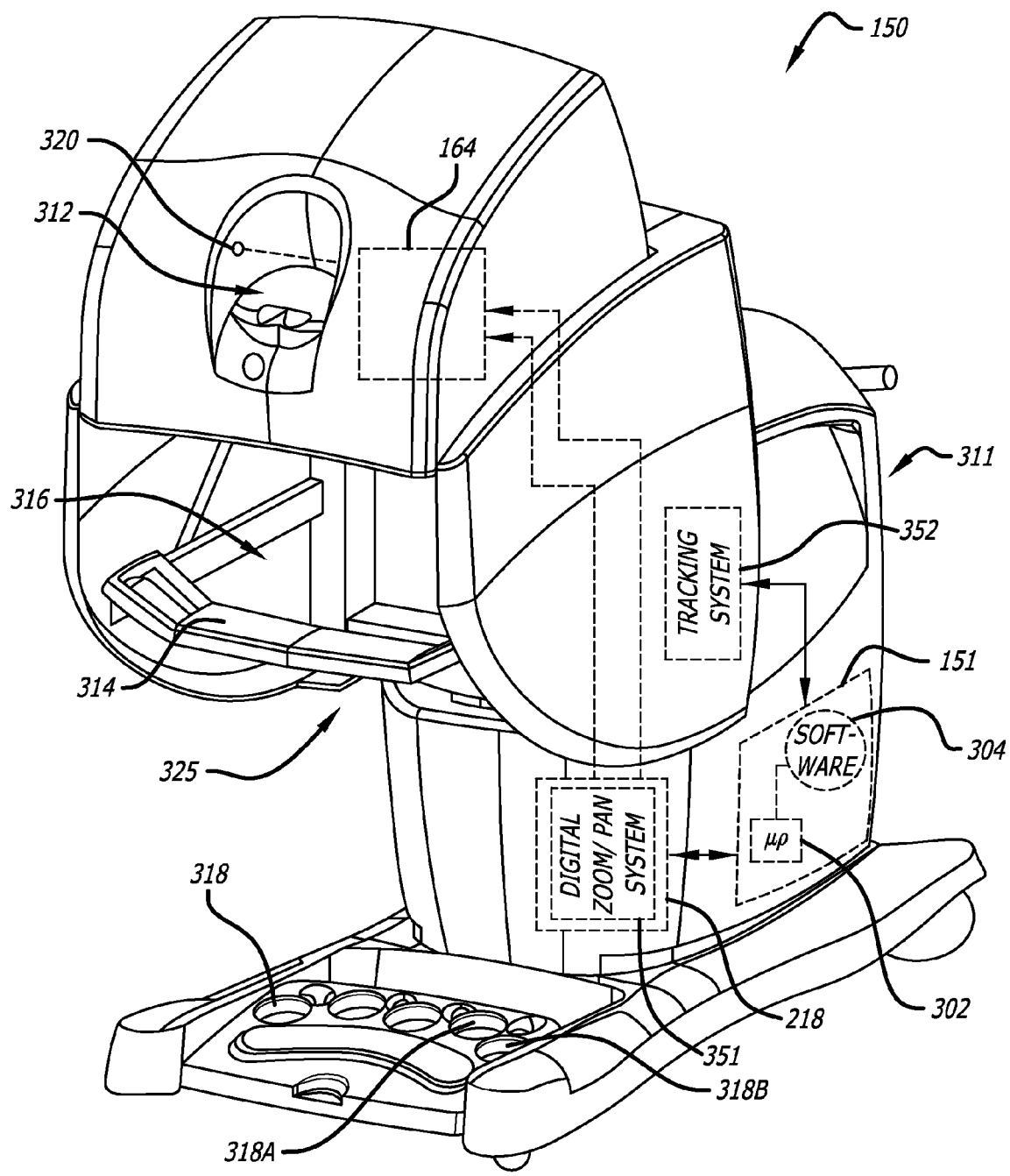
FIG. 3 is a perspective view of a robotic surgical master control console including a stereo viewer and an IGS system with tool tracking sub-system.

Referring now to FIG. 3, a perspective view of the robotic surgical master control console 150 is illustrated. The master control console 150 of the robotic surgical system 100 may include a computer 151, a stereo viewer 312, an arm support 314, a pair of control input wrists and control input arms in a workspace 316, foot pedals 318 (including foot pedals 318A-318B), and a head sensor 320. The master control console 150 may further include a digital zoom/panning system 351 and a tracking system 352 coupled to the computer 151 for providing the digital zoomed images, fovea images, and/or PIP images of the surgical site. The tracking system 352 may be a tool tracking system or a surgeon motion tracking system, such as for gaze detection/tracking, to provide for the digital panning of the camera images.

The stereo viewer 312 has two displays where stereo three-dimensional images of the surgical site may be viewed to perform minimally invasive surgery. When using the master control console, the operator O typically sits in a chair, moves his or her head into alignment with the stereo viewer 312 to view the three-dimensional images of the surgical site. To ensure that the operator is viewing the surgical site when controlling the robotic instruments 101, the master control console 150 may include a head sensor 320 disposed adjacent the stereo viewer 312. When the system operator aligns his or her eyes with the binocular eye pieces of the stereo viewer 312 to view a stereoscopic image of the surgical worksite, the operator's head activates the head sensor 320 to enable the control of the robotic instruments 101. When the operator's head is removed from the area of the stereo viewer 312, the head sensor 320 is deactivated to disable or stop generating new control signals in response to movements of the touch sensitive master control handles 160 in order to hold the state of the robotic instruments.

The arm support 314 can be used to rest the elbows or forearms of the operator O (typically a surgeon) while gripping touch sensitive master control handles 160 of the control input wrists, one in each hand, in the workspace 316 to generate control signals. The touch sensitive master control handles 160 are positioned in the workspace 316 disposed beyond the arm support 314 and below the viewer 312. This allows the touch sensitive master control handles 160 to be moved easily in the control space 316 in both position and orientation to generate control signals. Additionally, the operator O can use his feet to control the foot-pedals 318 to change the configuration of the surgical system and generate additional control signals to control the robotic instruments 101 as well as the endoscopic camera.

The computer 151 may include one or more microprocessors 302 to execute instructions and a storage device 304 to store software with executable instructions that may be used to generate control signals to control the robotic surgical system 100. The computer 151 with its microprocessors 302 interprets movements and actuation of the touch sensitive master control handles 160 (and other inputs from the operator O or other personnel) to generate control signals to control the robotic surgical instruments 101 in the surgical worksite. In one embodiment of the invention, the computer 151 and the stereo viewer 312 map the surgical worksite into the controller workspace 316 so it feels and appears to the operator that the touch sensitive master control handles 160 are working over the surgical worksite. The computer 151 may couple to the digital zoom/panning system 351 and the tracking system 352 to execute software and perform computations for the digital zoom/panning system.

Figure 4B:
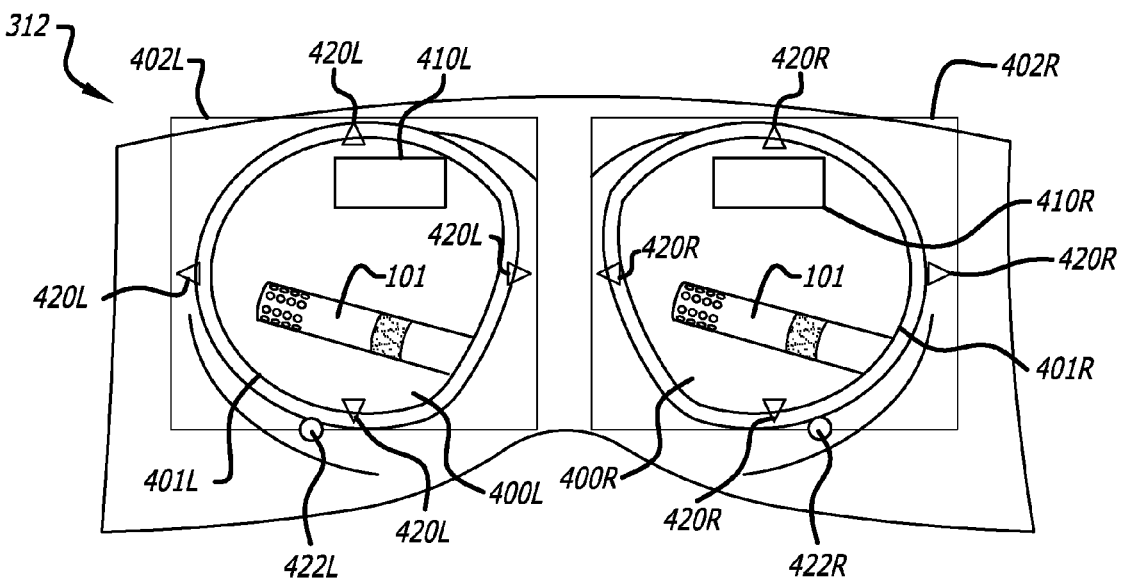
FIG. 4B is a perspective view of the stereo viewer with gaze detection in the robotic surgical master control console.

Referring now to FIG. 4A, a side cutaway view of the surgeon's master control console 150 is shown to illustrate the stereo viewer 312 with a gaze detection/tracking system. The stereo viewer 312 may include a left display 402L and one or more left gaze detection sensors 420L for the left eye EL of a surgeon and a right display 402R and one or more right gaze detection sensors 420R (not shown in FIG. 4A, see FIG. 4B) for the right eye of the surgeon. The head sensor 320 illustrated in FIG. 3 may be used to enable/disable the gaze detection system so that other motion is not inadvertently sensed as the surgeon's eye movement.

Figure 4C:
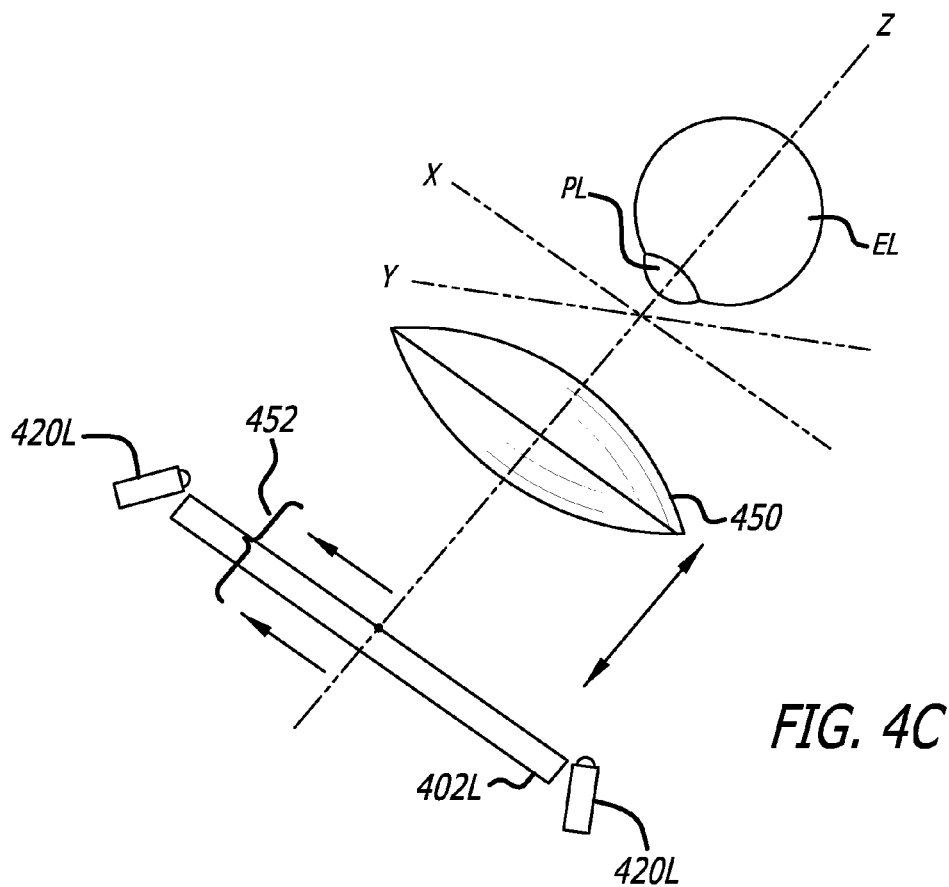
FIG. 4C is a side view of the stereo viewer with gaze detection in the robotic surgical master control console.

FIG. 4C illustrates a magnified side view of the stereo viewer 312 including the left display 402L and the one or more left gaze detection sensors 420L for the left eye EL of the surgeon. The one or more left gaze detection sensors 420L may sense X and Y axes movement of a pupil PL along a Z optical axis.

A fixed lens 450 may be provided between each eye and each respective display device 402L,402R to magnify or adjust the apparent depth of the displayed images I over a depth range 452. The focus on an image in the surgical site is adjusted prior to image capture by a moveable lens in the endoscopic camera 101B that is in front of the CCD image sensor.

Referring now to FIG. 4B, a perspective view of the stereo viewer 312 of the master control console 150 is illustrated. To provide a three-dimensional perspective, the viewer 312 includes stereo images for each eye including a left image 400L and a right image 400R of the surgical site including any robotic instruments 101 respectively in a left viewfinder 401L and a right viewfinder 401R. The images 400L and 400R in the viewfinders may be provided by a left display device 402L and a right display device 402R, respectively. The display devices 402L,402R may optionally be pairs of cathode ray tube (CRT) monitors, liquid crystal displays (LCDs), or other type of image display devices (e.g., plasma, digital light projection, etc.). In the preferred embodiment of the invention, the images are provided in color by a pair of color display devices 402L,402R, such as color CRTs or color LCDs.

In the stereo viewer 312, three dimensional images of a navigation window or a fovea may be rendered within the main image of the surgical site. For example, in the right viewfinder 401R a right navigation window image 410R may be merged into or overlaid on the right image 400R being displayed by the display device 402R. In the left viewfinder 401L, a left navigation window image 410L may be merged into or overlaid on the left image 400L of the surgical site provided by the display device 402L.

If the gaze detection system is used to control the position of the fovea or the digital panning of the digital zoom image of the surgical site, the stereo viewer 312 may include one or more left gaze detection sensors 420L near the periphery of the display device 402L for the left eye of the surgeon and one or more right gaze detection sensors 420R near the periphery of the display device 402R for the right eye of the surgeon. One of the gaze detection sensors for each eye may also include a low level light source 422L,422R to shine light into the eye of the surgeon to detect eye movement with the respective gaze detection sensors 420L,420R.

While a stereo video endoscopic camera 101B has been shown and described, a mono video endoscopic camera generating a single video channel of frames of images of the surgical site may also be used in a number of embodiments of the invention. Images, such as a navigation window image, can also be overlaid onto a portion of the frames of images of the single video channel.

Digital Zoom

As the endoscopic camera 101B is a digital video camera, it provides digital pixel information regarding the images that are captured. Thus, the digital images that are captured may be digitally zoomed in order to bring the objects closer in into view in the display of an image. In an alternate embodiment of the invention, the endoscopic camera 101B may include an optical zoom, in addition to a digital zoom, to magnify objects prior to image capture by using mechanical movement of optics, such as lenses.

In contrast to an optical zoom that involves a movement of optics, a digital zoom is accomplished electronically without any adjustment of the optics in the endoscopic camera 101B. Generally, a digital zoom selects a portion of an image and manipulates the digital pixel information, such as interpolating the pixels to magnify or enlarge the selected portion of the image. In other words, a digital zoom may crop a portion of an image and then enlarge it by interpolating the pixels to exceed the originally cropped size. While the cropped image may be larger, a digital zoom may decrease or narrow an apparent angle of view of the overall video image. To the surgeon, a digitally zoomed image alone may have a reduced field of view of the surgical site. Other images may be provided to compensate for the reduced field of view in the digitally zoomed image.

With some embodiments of invention, a region-of-interest is selected from source video images to undergo a digital zoom. The selected region of interest is then scaled linearly for presentation to the display (e.g., as a fovea 650). The region of interest may be scaled up (interpolated), or scaled down (decimated), depending on the number of pixels in the source region-of-interest, relative to the number of pixels allocated (for this tile of video) on the display. Digital filtering of the source data is performed as part of the interpolation/decimation process. Selection of a region-of-interest smaller than the full source video frame reduces the surgeon's effective field of view into a surgical site.

Note that there are four degrees of freedom available to a digital zoomed image in a rigid endoscope. The embodiments of the invention may pan a digital zoomed image up, down, left, and/or right and it may rotate the image and/or change its level of zoom.

As discussed previously herein, the endoscopic camera 101B is a high definition camera. In one embodiment of the invention, the high definition endoscopic camera 101B has a greater resolution than the resolution of the display devices 402L,402R. The extra pixel information from the high definition endoscopic camera 101B may be advantageously used for digital zoom. The region of interest selected from the source video need not be mapped one-to-one or magnified. In fact, a region of interest selected from the source video may contain more pixels than are allocated on the display for presentation of the video source. If that is the case, the pixels in the selected region of interest may be scaled down (decimated), while still appearing to the user to zoom in on objects.

Texture mapping, pixel mapping, mapping pixels, or mapping texture pixels, may be used interchangeably herein as functional equivalents where a source image is sampled at source coordinates or points (t_x,t_y) and a target image is colored at target coordinates or points (v_x,v_y).

As discussed previously, one aspect of some embodiments of the invention may be a linear digital zoom while one aspect of some embodiments of the invention may be a non-linear digital zoom.

Figure 5A:
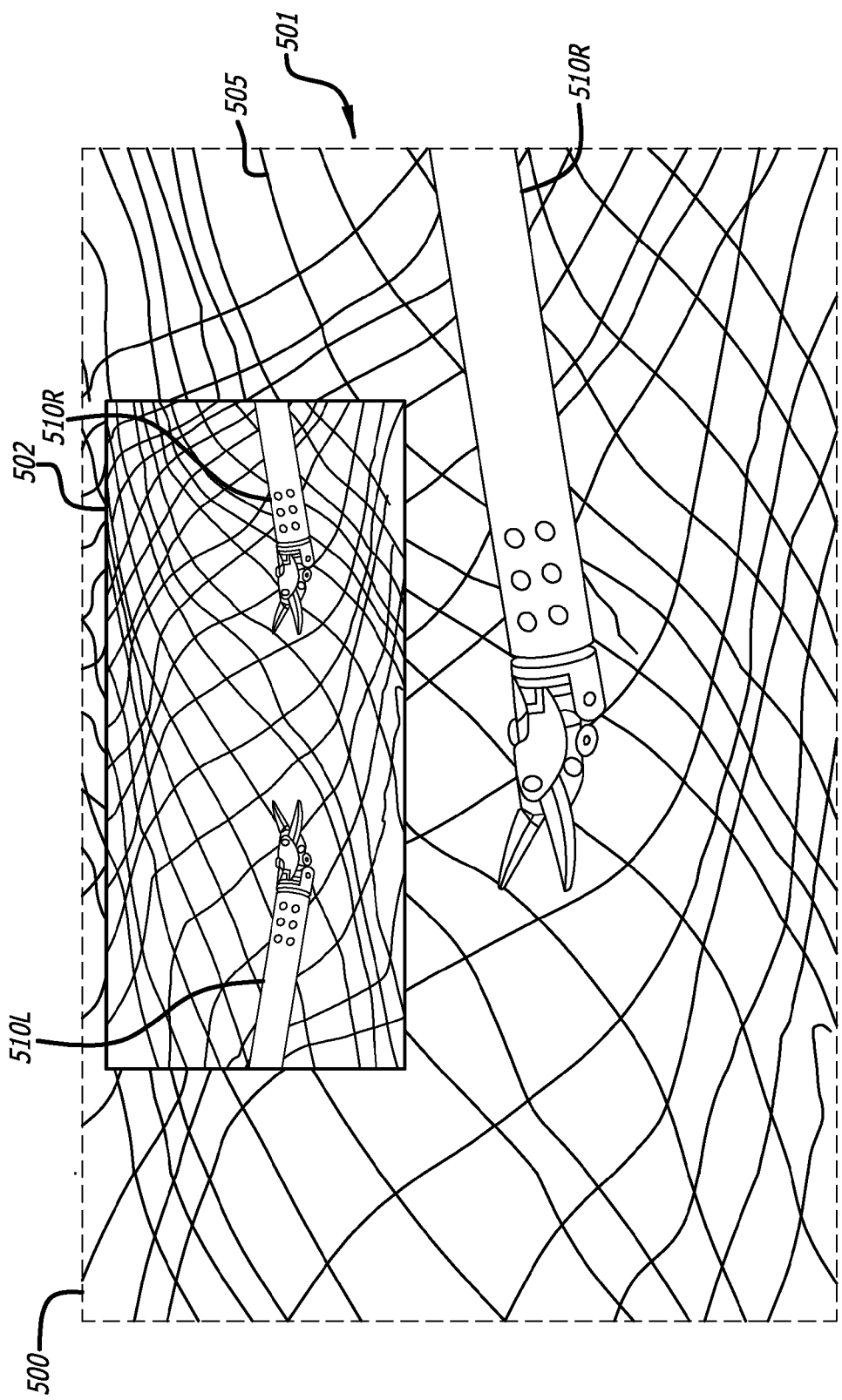
FIG. 5A is perspective view of a video frame including video images of a surgical site with a navigation window.

Referring now to FIG. 5A, a perspective view of images 500 in the stereo viewer 312 with a linear digital zoom is illustrated. A linear digital zoomed view 501 is displayed in a substantial portion of the display 402L,402R. The linear digital zoomed view 501 may magnify the images of tissue 505 and a right side surgical tool 510R in the surgical site. Alternatively, the view 501 may be a spatial subset of high definition images displayed on a portion of the display 402L,402R.

Within the linear digital zoomed view 501 may be a navigation window or pull-back view 502. The navigation window or pull-back view 502 may be the full spatial high definition image that has been down-sampled to be displayed picture-in-picture (PIP) within the smaller display region.

Figure 5B:
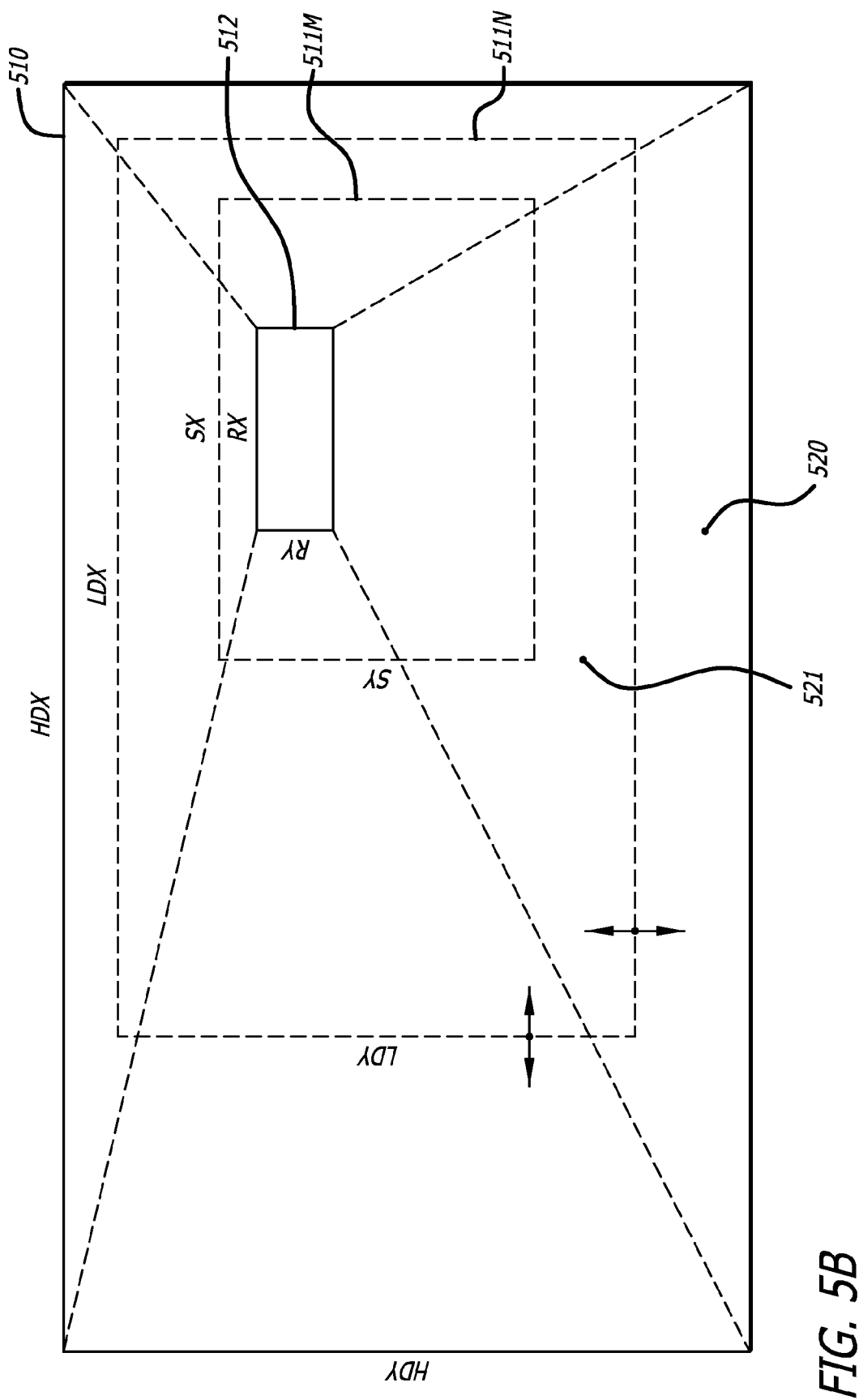
FIG. 5B is a schematic view of the video frame including video images of a surgical site with a navigation window.

Referring now to FIG. 5B, a pixel map diagram is illustrated for the linear digital zoomed view 501 of FIG. 5A. The stereo endoscopic camera 101B captures left and right high definition spatial images 510 with a two dimensional array of pixels that is HDX pixels wide by HDY pixels high. For example, the two dimensional array of pixels for the high definition spatial images 510 may be 1920 pixels wide by 1080 pixels high.

However, the display devices 402L,402R in the stereo view 312 may only display low definition images 511N with a two-dimensional array of pixels with a native resolution of LDX pixels wide by LDY pixels high that are respectively less than the available spatial resolution of HDX pixels wide by HDY pixels high for the high definition spatial images 510. For example, the two dimensional array of pixels for the low definition spatial images 511N may be 1280 pixels wide (LDX) by 1024 pixels high (LDY) in contrast to 1920 pixels wide (HDX) by 1080 pixels high (HDY) for exemplary high definition spatial images 510.

As the display devices 402L,402R in the stereo viewer 312 display a lower native resolution of LDX pixels wide by LDY pixels high, some of the pixel information in the full spatial high definition image 510 may go unused. For example, the position and relationship between the low definition images 511N and the high definition images 510 may be fixed. In which case, pixels 521 within the resolution of the low definition image 511N may be displayed on the display devices 402L,402R while some pixels 520 outside the resolution of the low definition image 511N may not be displayed. In this case, the display devices may be considered as providing a field of view of a virtual camera inside the endoscopic camera.

The field of view of the virtual camera within the field of view of the endoscopic camera may be digitally adjusted. That is, the pixels in the high definition images 510 that are to be displayed by the display devices 402L,402R may be user selectable. This is analogous to the low definition image 511N being a window that can be moved over the array of HDX by HDY pixels of the high definition spatial image 510 to select an array of LDX by LDY pixels to display. The window of the low definition image 511N may be moved in X and Y directions to select pixels in the array of HDX by HDY pixels of the high definition spatial image 510. The pixels in the high definition images 510 that are to be displayed by the display devices 402L,402R may also be digitally manipulated.

A smaller subset of pixels (SX by SY) in the array of HDX by HDY pixels of the high definition spatial image 510 may be respectively selected by a user for magnification into a digital zoom image 51M. The array of SY pixels high by SX pixels wide of the digital zoom image 511M may be interpolated with a digital filter or sampling algorithm into a larger number of pixels of the array of LDX by LDY pixels to display a magnified image on the display devices 402L,402R. For example, 840 pixels wide by 672 pixels high may be magnified and expanded to 1280 pixels wide by 1024 pixels high maintaining the same aspect ratio for display, such as on the display devices 402L,402R.

While the digital zoom image 511M may be expanded by interpolation into a larger number of pixels to display a magnified image, such as image 501 illustrated in FIG. 5A, the image resolution of the array of HDX by HDY pixels of the high definition spatial image 510 may decimated or reduced down (down-sampled) to shrink or demagnify its image to fit into a window array 512 of reduced pixels RX pixels high by RY pixels wide to be used for the navigation window 502 illustrated in FIG. 5A. For example, high definition spatial images 510 with an array of 1920 pixels wide by 1080 pixels high may be decimated by a factor of ten to a demagnified image array of 192 pixels wide by 108 pixels high.

While the digital zoom for a portion of the display may have a linear relationship with the pixels of the full spatial image, the digital zoom may also have a non-linear relationship with the pixels of the full spatial image in another portion of the display device.

Referring now to FIG. 6A, a perspective view of an image 600 in the stereo viewer 312 with is illustrated. A digital zoomed portion (fovea) 650 is displayed within a background or surround portion 651 of the image 600 on the display devices 402L,402R. As the digital zoomed view 650 may be the focus of the central vision of a surgeon's eyes and surrounded by the surround 651, the digital zoomed view 650 may also be referred to as a fovea 650. The digital zoomed view 650 may be considered to be a virtual image within a larger image analogous to the virtual camera within the endoscopic camera.

Figure 6B:
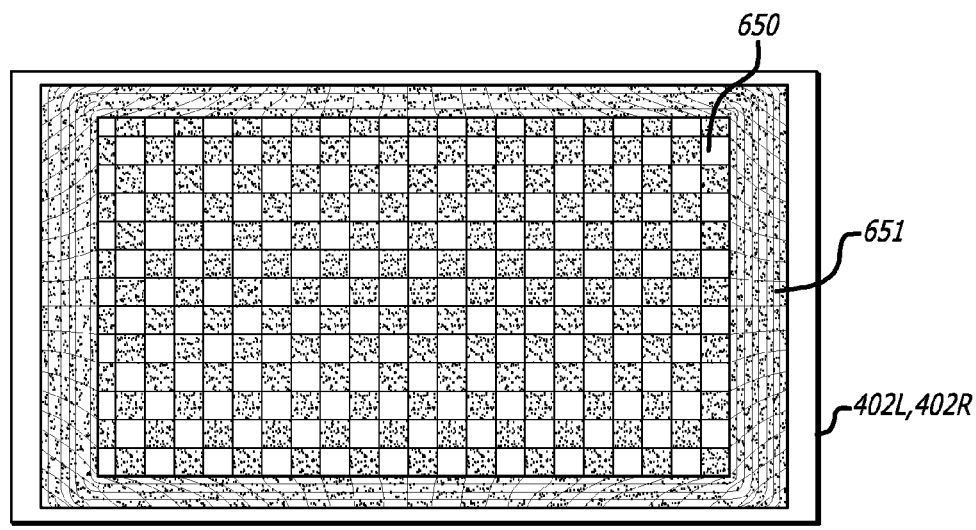
FIG. 6B is an exemplary illustration of a linear mapping between source pixel information and target pixels for a digitally zoomed fovea of a display and a non-linear mapping between source pixel information and target pixels for a background or surround image portion of the display.

In FIG. 6A, the digital zoomed view 650 is moveable around the display (moveable fovea) and may magnify the images of tissue 605 and surgical tools 610R in the surgical site. In another configuration, the digital zoomed view or fovea 650 is centrally fixed in position (fixed fovea) within the center of the display device (e.g., see FIG. 6B). While the fovea may provide a digitally zoomed image or view of the surgical site, the background or surround image 651 may provide an improved sense of peripheral vision to the surgeon, possibly reducing or eliminating the need for one or more navigation windows.

The fovea 650 is formed by a first mapping of first array or set of source pixel information (source pixels) from the high definition source video images to a first array or set of pixels in the display device (target pixels). The surround 651 around the fovea 650 is formed by a second mapping of a second array or set of source pixel information (source pixels) from the high definition source video images to a second array or set of pixels in the display device (target pixels).

The second mapping differs from the first mapping. In one embodiment of the invention, the first mapping is a linear mapping and the second mapping is a non-linear mapping (e.g., see FIG. 6B). In another embodiment of the invention, the first mapping and the second mapping are linear mappings (e.g., see FIG. 6F) but differ in other ways, such as size and/or resolution. For example, the digital zoomed view 650 may be a high resolution or high definition image while the background or surround image 651 is a low resolution or low definition image.

The digital zoomed view 650 and the background or surround portion 651 of the image 600 are displayed in real time to a surgeon over a continuing series of video frame images on the displays 402L,402R of the stereo viewer. The images may be continuously updated to view current tool positions and current state of the surgical site and any tissue that is being manipulated therein.

At its edges, there may be a sharp or gradual transition from the digital zoomed view 650 to the background or surrounding image 651. For ease of discussion herein, a sharp or hard edge between the fovea 650 and the background 651 may be assumed.

The digital zoomed view 650 may be provided by a linear digital zoom factor over the given field of view selected by a surgeon to reduce distortion of the image displayed in the fovea 650. The surround view or image 651 may be provided by a linear digital zoom factor (linear mapping) or a non-linear digital zoom factor (non-linear mapping) over the given field of view selected.

The size of the digital zoom view 650 within the image 600 may be user selectable by a surgeon at the master control console 150 or by an assistant at the external display 154. That is, a user may selectively expand or contract the x-axis FX and the y-axis FY pixel dimensions of the area of the fovea or linear digital zoom view 650. The digital zoom view 650 may be centered in the display to be in line with a central gaze of the surgeon's eyes. Alternatively, a user may selectively position the linear digital zoom view 650 within different positions on the display within the image 600 by different user interface means described herein.

Additionally, the source region-of-interest (source zoom pixels) selected for the fovea 650 from the high definition source video images and the source region-of-interest (source background pixels) selected from the high definition source video images for the surround 651 may be adjusted by the user. For example, the source pixels for the background around the fovea 650 may selected to be a spatial subset of the high definition source images. Alternatively, the source pixels for the background 651 may be selected to be a set of source pixels to complete the full spatial image of the high definition images. With a larger field of view provided by the background 651 around the fovea 650, a surgeon's peripheral vision of the surgical site may be improved. This can help avoid or reduce frequent short duration camera control events that otherwise may be made due to a desire to see what's just outside the field of view.

As discussed previously, the fovea 650 is formed by a first mapping of array or set of source pixel information (source pixels) from the high definition source video images to a first array or set of pixels in the display device (target pixels) and the surround 651 is formed by a second mapping of a second array or set of source pixel information (source pixels) from the high definition source video images to a second array or set of pixels in the display device (target pixels).

Figure 6C:
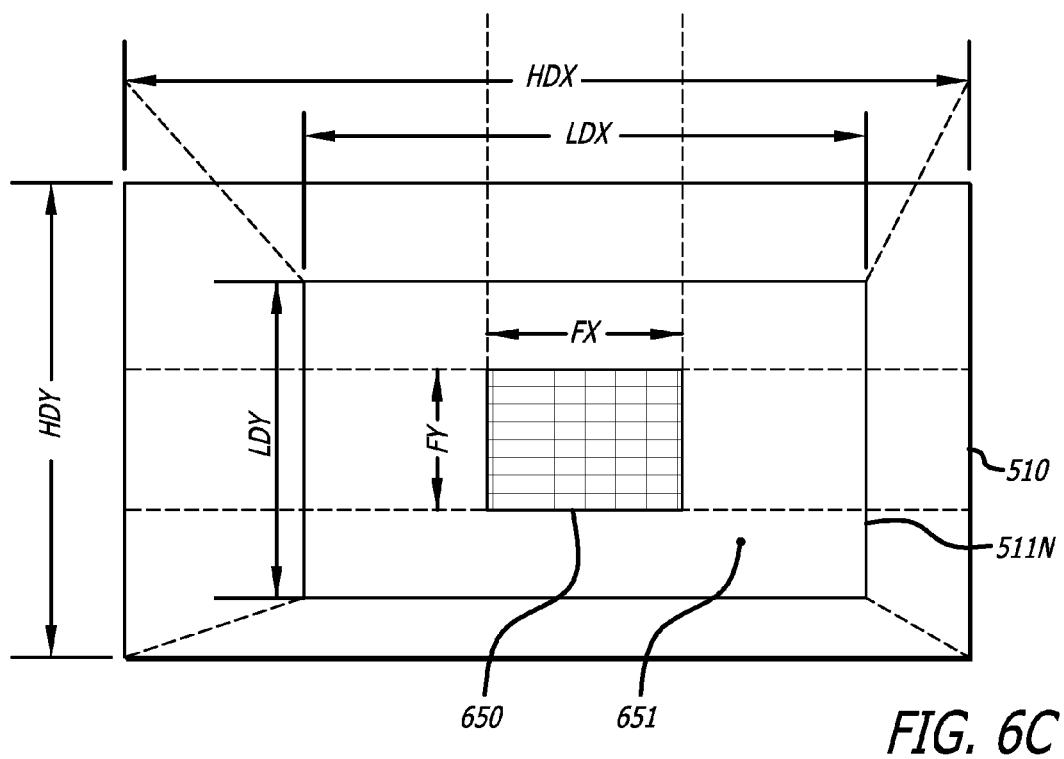
FIG. 6C is a schematic diagram illustrating of a linear mapping between source pixel information and target pixels for a digitally zoomed fovea of a display and a linear mapping between source pixel information and target pixels for a background or surround image portion of the display.
Figure 6D:
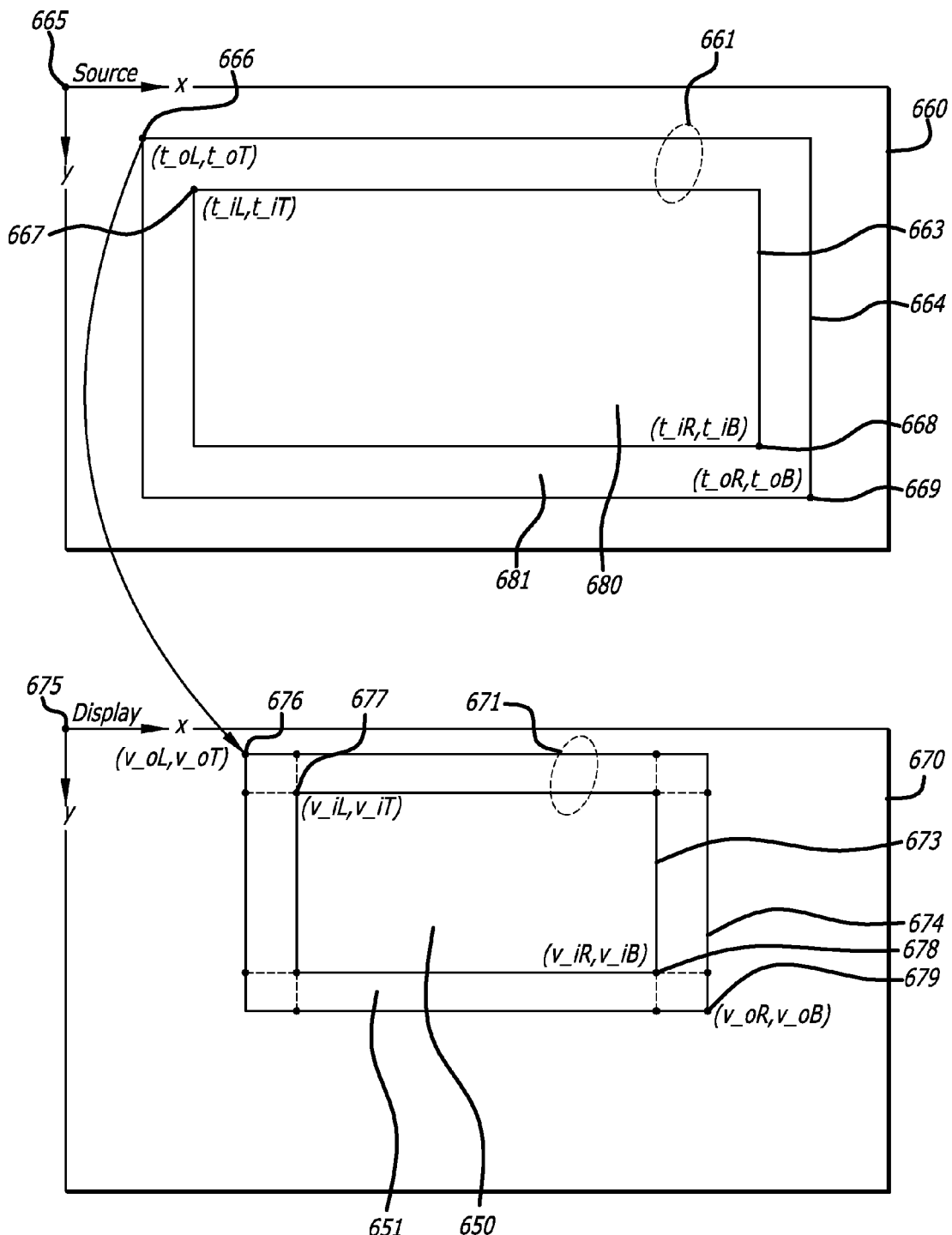
FIG. 6D is a schematic diagram illustrating a mapping between source pixel information and target pixels of a display.

Referring now to FIG. 6D, mapping functions for the first and second pixel mappings are determined between coordinates in the source (texture) 660 and coordinates on the target 670 (e.g., display 402L,402R,154). Pixel data is mapped from an inner/outer pair of source windows 661 to an inner/outer pair of target windows 671.

The source coordinate system origin 665 is defined to be the upper left corner of the source frame 660 with positive-x right, and positively down. The inner source window 663 may be defined by selection of a left-top coordinate (t_iL,t_iT) 667 and a right-bottom coordinate (t_iR,t_iB) 668. The outer source window 664 may be defined by its left-top coordinate (t_oL,t_oT) 666 and right-bottom coordinate (t_oR,t_oB) 669. In the parenthetical coordinate description, the prefix t denotes texture, i/o refers to inner/outer, and L,T,R,B refers to left, top, right, and bottom, respectively. The coordinates for the inner source window 663 and the outer source window 664 may be directly or indirectly and automatically or manually selected by a user (e.g., surgeon O or assistant A) in a number of ways.

The target coordinate system origin 675 is defined to be the upper left corner of the target frame 670, with positive-x right and positively down. The inner target window 673 is defined by its left-top coordinate (v_iL,v_iT) 677 and its right bottom coordinate (v_iR,v_iB) 678. The outer target window 674 is defined by its left-top coordinate (v_oL,v_oT) 676 and its right-bottom coordinate (v_oR,v_oB) 679. In the parenthetical coordinate description, the prefix v denotes vertex, i/o refers to inner/outer, and L,T,R,B refers to left, top, right, and bottom, respectively. The coordinates for the inner target window 673 and the outer target window 674 may also be directly or indirectly and automatically or manually selected by a user (e.g., surgeon O or assistant A) in a number of ways.

Figure 6E:
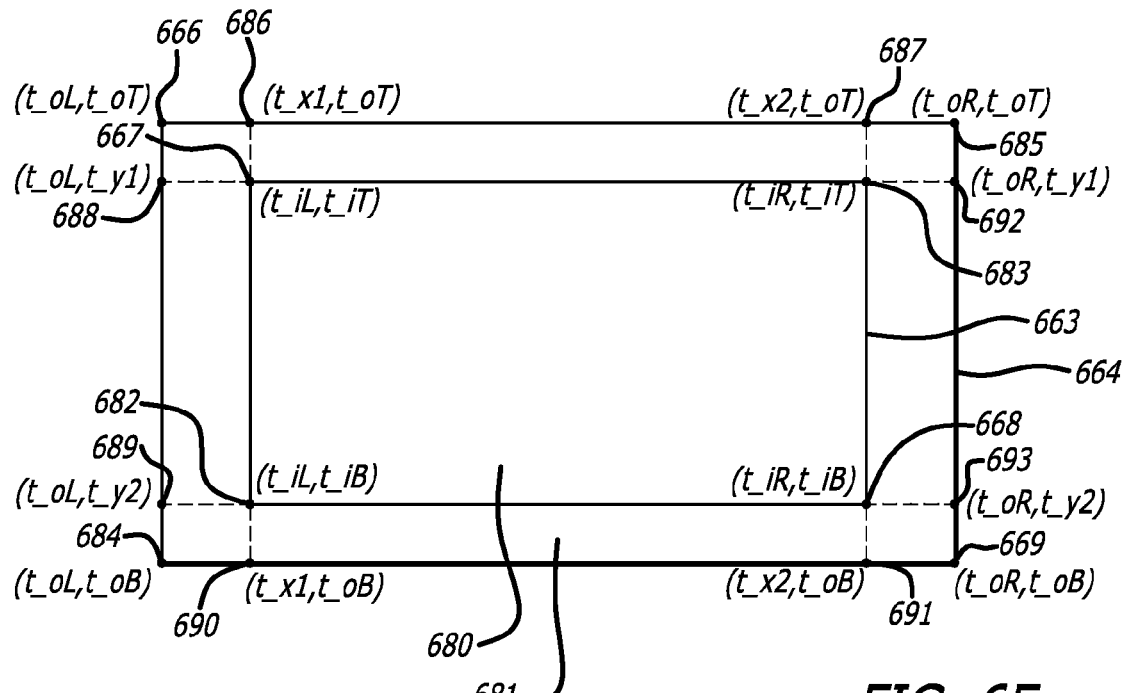
FIG. 6E is a schematic diagram illustrating the inner and outer source pixel windows of FIG. 6D.

Referring now to FIGS. 6D-6E, the region corresponding to the fovea 650 is simply formed by linearly scaling the source pixel array 680 of the inner source window 663 from coordinate (t_iL,t_iT) 667 through coordinate (t_iR,t_iB) 668 into the target pixel array (fovea) 650 of the inner target window 673 from coordinate (v_iL,v_iT) 677 through coordinate (v_iR,v_iB) 678. Constructing the surround region 651 around the fovea 650 remains.

The task of mapping source pixels in the frame shaped region 681 between the inner source window 663 and the outer source window 664 into target pixels in the frame shaped surround region 651 between the inner target window 673 and the outer target window 674 is more difficult due to the frame like shape of each.

Referring now to FIG. 6E, the source pixels in the frame shaped region 681 between the inner source window 663 and outer source window 664 is subdivided into a number of N rectangular regions (quads). The N rectangular regions may be eight (8) rectangular regions, for example. Starting at the upper left hand corner and working clockwise, the eight rectangular regions may be formed by coordinates 666,686,667,688; 686,687,683,667; 687,685,692,683; 683,692,693,668; 668,693,669,691; 682,668,691,690; 689,682,690,684; and 688,667,682,689. Values for t_x1, t_x2, t_y1, and t_y2 in the coordinate (t_x1,t_oT) 686, coordinate (t_x2,t_oT) 687, coordinate (t_oL,t_y1) 688, coordinate (t_oL,t_y2) 689, coordinate (t_x1,t_oB) 690, coordinate (t_x2,t_oB) 691, coordinate (t_oR,t_y1) 692, and coordinate (t_oR,t_y2) 693 are determined which allow the subdivision of the frame shaped surround region 681 into the 8 rectangular regions (quads).

Referring now to FIGS. 6D-6E, if the source pixels t_oL through t_oR on top and bottom edges of outer source window 664 are mapped linearly into the target pixels v_oL through v_oR on top and bottom edges of outer target window 674, then the values of t_x1 and t_x2 are respectively proportional to the length of the line segments from pixels v_oL through v_iL and pixels v_oL through v_iR along top and bottom edges of the outer source window 664, and may be computed by equations 1 and 2 as follows:

$$t\_x1 = t\_oL + (t\_oR - t\_oL)*((v\_iL - v\_oL)/(v\_oR - v\_oL)) \quad (1)$$

$$t\_x2 = t\_oL + (t\_oR - t\_oL)*((v\_iR - v\_oL)/(v\_oR - v\_oL)) \quad (2)$$

Similarly, if the source pixels t_oT through t_oB on the right and left edges of outer source window 664 are mapped linearly into the target pixels v_oT through v_oB on left and right edges of outer target window 674, then the values of t_y1 and t_y2 are respectively proportional to the length of the segments from pixels v_oT through v_iT, and pixels v_oT through v_iB along left and right edges of the outer source window 664. Thus, the values of t_y1 and t_y2 may be computed by equations 3 and 4 as follows:

$$t\_y1 = t\_oT + (t\_oB - t\_oT)*((v\_iT - v\_oT)/(v\_oB - v\_oT)) \quad (3)$$

$$t\_y2 = t\_oT + (t\_oB - t\_oT)*((v\_iB - v\_oT)/(v\_oB - v\_oT)) \quad (4)$$

Thus, the source pixels along the edges of the quads may be mapped with a predetermined mapping (e.g., equations 1-4) into target pixels values.

For each interior pixel point (v_x,v_y) in the surround 651 of each quad of the N quads in the source frame 681, we may perform an interpolation to map source pixels into respective t_x and t_y values of the target pixels. The interpolation may be a non-linear interpolation, such as a bilinear interpolation (BI), or a linear interpolation, where the selection of the interpolation function is arbitrary. At larger zoom factors of the fovea 650, a non-linear interpolation may distort less than a linear interpolation.

A quad drawn counter-clockwise, has target vertex coordinates defined as:
 LowerLeft: v_L, v_B
 Lower Right: v_R, v_B
 Upper Right: v_R, v_T
 Upper Left: v_L, v_T
and associated source texture coordinates defined as:
 Lower Left: t_LLx, t_LLy
 Lower Right: t_LRx, t_LRy Upper Right: t_URx, t_URy
Upper Left: t_ULx, t_ULy For each interior target point v_x,v_y within each quad, the associated source texture point t_x, t_y is found by interpolation. With the source texture point or coordinate being known for the source pixel, the texture of the source texture point can be sampled using an arbitrary filter function and the target pixel at the target coordinate can be colored with the sampled value of texture. That is, the source texture is sampled at coordinate (t_x,t_y) using a filter function to color the target pixel (v_x,v_y). The filter function used in the sampling process may be arbitrarily complicated but consistently used.

Assuming that a bilinear interpolation (BI) is performed for each interior pixel point (v_x,v_y) in the surround 651, we may perform a bilinear interpolation (BI) into respective t_x and t_y values (generally referred to as t values) which are specified on the quad boundary by equations 5 and 6 as:

$$t\_x = BI[v\_x, v\_y; v\_L, v\_T, v\_R, v\_B; t\_LLx, t\_LRx, t\_URx, t\_ULx] \quad (5)$$

$$t\_y = BI[v\_x, v\_y; v\_L, v\_T, v\_R, v\_B; t\_LLy, t\_LRy, t\_URy, t\_ULy] \quad (6)$$

where t_x and t_y are the interpolated t values at each point (v_x,v_y); v_L,v_T, v_R,v_B are target boundary coordinates; and t_LLx,t_LRx,t_URx,t_ULx are the lower-left, lower-right, upper-right, and upper-left 't' coordinates in x and t_LLy,t_LRy,t_URy,t_ULy are the lower-left, lower-right, upper-right, and upper-left 't' coordinates in y. A bilinear interpolation (BI) is an interpolating function of two variables on a regular grid. With the values of t_x1, t_x2, t_y1, and t_y2 being known from equations 1-4, there are known coordinates 686-692 along the edges of the outer source window 664 that may be used as known points for the interpolation within each of the N quads.

The bilinear interpolation BI( ) may be defined in pseudo code as:

```
BI(v_x,v_y, v_L,v_T,v_R,v_B, t_LL,t_LR,t_UR,t_UL)
{
  a1 = lerp(v_x, v_L, v_R, t_LL, t_LR);
  a2 = lerp(v_x, v_L, v_R, t_UL, t_UR);
  b1 = lerp(v_y, v_T, v_B, a2, a1); // NOTE: swap a2,a1 due to
  Y+ downward
  return(b1);
}
``` with lerp( ) being defined in pseudo code as:

```
lerp(v, v1, v2, q1, q2)
{
  return( q1*((v2−v)/(v2−v1)) + q2*((v−v1)/(v2−v1)) );
}
```

A bilinear interpolation (BI) is a well known non-linear mathematical function. It is non-linear as it is mathematically proportional to a product of two linear functions such as $(a_1 x + a_2)(a_3 y + a_4)$. In this case, the bilinear interpolation is a combination of multiple linear interpolations over a grid to smoothly transition images between the inner and outer areas of interest of the source windows 661 and target windows 671. The bilinear interpolation results in a quadratic warp in the surround 651 around the fovea 650.

For example in FIG. 6E, consider the upper left quad of source pixels in the source frame 681 and mapping them into upper left quad of the surround 651. The source texture coordinates assigned to each of the four vertices of the quad of source pixels is determined in accordance with equations 1-4 described herein. For the upper left quad the following mapping of vertices is determined:

(t_oL,t_y1) maps to (v_oL,v_y1)

(t_iL,t_y1) maps to (v_iL,v_y1)

(t_iL,t_oT) maps to (v_iL,v_oT)

(t_oL,t_oT) maps to (v_oL,v_oT)

Then the texture coordinate (t_x,t_y) of each pixel interior to the quad at position (v_x,v_y) is found via bilinear interpolation. The source texture is sampled at coordinate (t_x,t_y) to color the pixel (v_x,v_y) with an arbitrary filter function.

Each of the N quads is similarly processed once the texture coordinates have been assigned to its vertices. As adjacent quads have the same texture coordinates assigned to their shared vertices, the final image appears to be a smooth warp, without discontinuity across quad-boundaries.

Referring now to FIG. 6B, the results of a first linear mapping of a checkerboard pattern into the fovea 650 and a non-linear mapping (e.g., using bilinear interpolation) of a checkerboard pattern into eight quads of the surround 651 are illustrated. Lines in the checkerboard of the source image illustrated on the display indicate warped pixel information. As the lines are straight and equidistant in the fovea 650, it is digitally zoomed without any mapping distortion being added. The surround 651 experiences some warping as it changes from the digitally zoomed (magnified) image at the edge of the fovea 650 to a lower digitally zoomed (magnified) image at the outer edges of the surround. The warpage in the surround 651 is more noticeable at the corners of the fovea in the FIG. 6B as indicated in the bending lines in the checkerboard.

Instead of a non-linear mapping between source pixels and the target pixels in the N quads of the source frame 681, a linear mapping may be used but differs from the linear mapping of pixels for the fovea 650. The mapping of the source pixels in the source frame 681 to the target pixels in the surround 651 is piecewise linear for the N quads if the values of t_x1, t_x2, t_y1, and t_y2 are set as follows:

t_x1=t_iL;
t_x2=t_iR;
t_y1=t_iT;
t_y2=t_iB;

That is, each of the pixels in the N quads is linearly mapped with a linear scaling function into pixels in the surround 651.

Figure 6F:
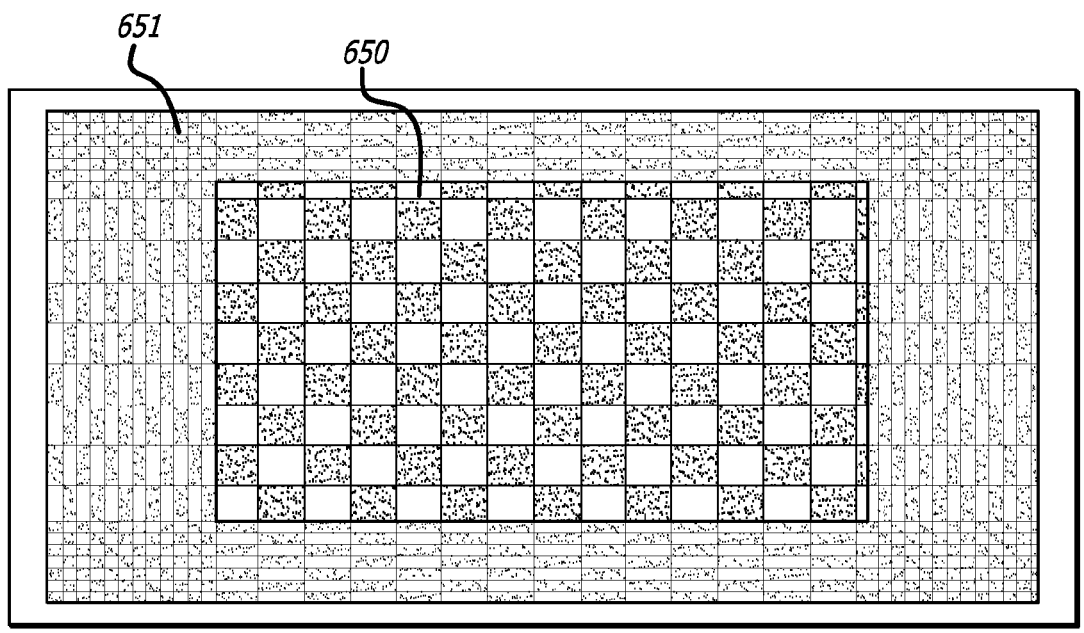
FIG. 6F is an exemplary illustration of a linear mapping between source pixel information and target pixels for a digitally zoomed fovea of a display and a linear mapping between source pixel information and target pixels for a background or surround image portion of the display.

Referring now to FIG. 6F, the results of a first linear mapping of a checkerboard pattern into the fovea 650 and a second linear mapping (e.g., piecewise linear) of a checkerboard pattern into eight quads of the surround 651 are illustrated. At relatively low digital zoom factors for the fovea 650, the surround 651 shows only nominal warpage. However if a relatively high digital zoom factor is applied to the fovea 650 to highly magnify objects in the fovea 650, the surround 651 with no change in digital zoom factor experiences significant warpage. Thus, it has been determined that a non-linear mapping between source pixels of the frame 681 to target pixels in the surround 651 is preferable.

Note that the resolution of the fovea 650 and the surround 651 depends upon the selection of the relative sizes of the inner/outer source regions and the selection of the relative sizes of the inner/outer display or target regions. If a user selects to digitally zoom the fovea 650, the size of the inner source window 663 is typically decreased by changing a digital zoom factor magnifying the image in the fovea 650. In this case, the size of the frame 681 of the source video will change resulting in a change in the warp of the surround 651 as well.

With the first and second mappings determined from source to target for the fovea 650 and the surround 651, various digital filter methods and resampling algorithms may then be used to sample the source pixel texture information for interpolation/decimation into the target pixels of one or more display devices. Exemplary digital filters that may be used are a box filter, tent filter, Gaussian filter, sinc filter, and lanczos filter.

Referring now to FIG. 6C, a schematic diagram illustrates another linear mapping of source pixels from the high definition video source images of the endoscopic camera to target pixels of the display are shown to further explain a linear mapping of the fovea 650 and a linear mapping of the surround or background 651.

As discussed previously with reference to FIG. 5B, the high definition spatial images 510 have a two dimensional array of pixels that is HDX pixels wide by HDY pixels high. For example, the two dimensional array of pixels for the high definition spatial images 510 may be 1920 pixels wide by 1080 pixels high. The display devices 402L, 402R in the stereo viewer 312 may display lower native resolution images 511N with a two-dimensional array of pixels having a native resolution of LDX pixels wide by LDY pixels high. The dimensions LDX pixels wide and LDY pixels high of the lower native resolution images 511N are respectively less than the available spatial resolution of HDX pixels wide and HDY pixels high for the high definition spatial images 510.

The fovea 650 may be an image having dimensions FX pixels wide (X-axis pixels) and FY pixels high (Y-axis pixels) of the high definition image without interpolation or decimation such that there is no loss of resolution or detail in the display area of interest to a surgeon. In this case there is a one to one mapping between pixels of the high definition image and pixels of the lower resolution display. However, extra pixels to each side of the fovea 650 need to be compressed or decimated down to fewer pixels in the display.

For example, the high definition spatial images 510 are 1920 pixels wide (X-axis pixels) by 1080 pixels high (Y-axis pixels) and the native pixel dimensions of the display (low definition spatial images 511N) are 1280 pixels wide (X-axis pixels) by 1024 pixels high (Y-axis pixels). Consider in this case that the fovea 650 is an image having dimensions of 640 pixels wide (FX) and 512 pixels high (FY) (Y-axis pixels) to be placed in the center of the display. An array of 640 pixels wide (X-axis pixels) and 512 pixels high (Y-axis pixels) in the high definition image 510 is mapped one to one into the 640 pixels wide (FX) (X-axis pixels) and 512 pixels high (FY) (Y-axis pixels) in the fovea 650. This leaves 640 pixels wide (X-axis pixels) in the high definition image 510 to each side of the fovea to be respectively mapped into 320 pixels wide (X-axis pixels) to each side of the fovea in the display image 511N resulting in a two-to-one decimation if the full spatial image is to be displayed. Thus, a two-to-one decimation or compression in resolution maps the remaining X-axis pixels of the high definition image into the remaining X-axis pixels of the background or surround 651. Continuing with the Y-axis pixels, 284 pixels high (Y-axis pixels) in the high definition image 510 above and below the fovea are to be respectively mapped into 256 pixels high (Y-axis pixels) above and below the fovea in the display image 511N if the full spatial image is to be displayed. Thus, approximately a 1.1-to-1 decimation or compression in resolution along the Y-axis maps the remaining Y-axis pixels of the high definition image into the remaining Y-axis pixels of the background or surround 651. Note that this assumes a total linear mapping in the surround 651, not a piece-wise linear in each of N quads, which may not work well in the corners.

Note that with the total linear mapping in the surround 651 described with reference to FIG. 6C, the Y-axis compression or decimation may differ from the X-axis compression or decimation. In this case, the image in the surround will be distorted by being compressed differently along the axis with the greater decimation. In the case of the mappings illustrated by FIGS. 6D-6E, the source/target windows are defined as a percentage of the source/target extent. Thus, the raw number of pixels in the surround 651 differs in X,Y, but the percentage change between the inner/outer windows is the same resulting in less distortion.

If the display is a high definition display with the same resolution of high definition special images of the endoscopic camera, the background 651 may be displayed at the native resolution while the fovea 650 is interpolated up to be a magnified image within its pixel array of FX by FY pixels.

Automatic Digital and Mechanical Image Panning

In one embodiment of the invention, the fovea 650 may be fixed in the center of the display image 511N and the center of the display device. If the outer-source-window is smaller than the source extent, the inner/outer source windows may be digitally panned within the source frame. In this manner, inner/outer source window and the inner/outer target windows are concentric to minimize distortion in the background/surround 651 around the fovea 650.

Alternatively in another configuration, the fovea 650 may be digitally (or electronically) moved within the display image 511N by various means in response to an automatically sensed signal or a manually generated signal. That is, the fovea 650 may be digitally (electronically) panned around within the display image. This may be accomplished by changing the coordinates defining the fovea 650 in the mapping of source pixels to target pixels in the display. In this case, the inner/outer source window and the inner/outer target windows may not be concentric.

In either case, if an image is digitally panned without any mechanical panning of the endoscopic camera, the surgeon's perspective (angle at which the surgical site is viewed) on the surgical site is unchanged.

In the case of the moving fovea, if the fovea 650 nears the edge of the display image 511N, a centralization process may occur where the pixels of the display image 511N may adjust to position the fovea 650 more centrally in the display image 511N. Moreover if the desired location of fovea 650 is outside the matrix of pixels in the display image 511N, the display image 511N may digitally adjust its position within the high definition spatial image 510 by selecting different pixels within the high definition spatial image 510. This is analogous to a virtual camera moving around in the high definition spatial image 510. In this case, both the fovea 650 and the display image may be digitally (electronically) panned around within the matrix of pixels of the high definition spatial image 510.

In the alternate embodiment of the invention where the fovea 650 is fixed in the center of the display, the source window for selecting the source of pixel information in the high definition video source images moves to recenter the source area of interest within the fovea and the center of the display in a substantially instantaneous manner.

Further more, if the desired location of fovea 650 not only exceeds the pixels in the display image 511N but also the pixels of the high definition spatial image 510, the endoscopic camera 101B may be mechanically moved by the motors in the robotic arm 158B to adjust the field of view of the surgical site in response thereto. In this case, the fovea 650 and the display image may be digitally (electronically) panned while the endoscopic camera 101B is mechanically panned to change the field of view of the surgical site. In alternate embodiment of the invention, the endoscopic camera 101B may be slewed slowly both digitally (electronically) and mechanically (physically) to maintain the source area of interest substantially centered in the source video frame. If the source area-of-interest is moved off-center, the endoscopic camera 101B may be mechanically moved and concurrently the source window may be digitally moved in the opposite direction until the source-window is re-centered relative to the full-extent of the source video captured by the endoscopic camera.

Reference is now made to FIGS. 7A-7D to illustrate digital panning of images and both digital and mechanical panning.

Figure 7A:
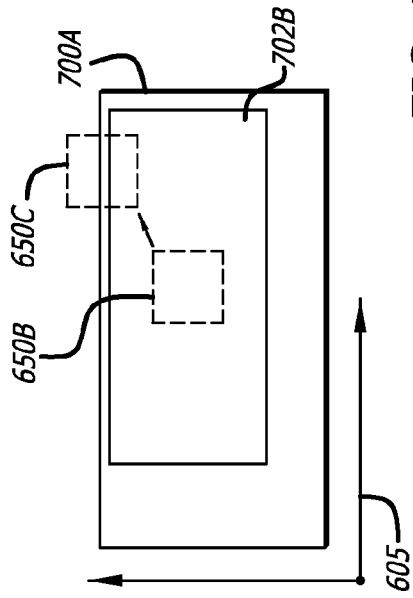
FIGS. 7A-7D are diagrams to illustrate combinations of digital pan and/or mechanical panning of the endoscopic camera of a frame of a video information with a digital zoom portion in response to gaze detection.

In FIG. 7A, an initial fovea position 650A of the fovea 650 is shown centered in an image 702A on a display 402L,402R. The pixels of image 702A displayed by the display may be centered with respect to the pixels of a high definition spatial image 700A providing the endoscopic camera 101B field of view.

A surgeon or an assistant may desire to move the fovea 650 from the initial fovea position 650A to a different fovea position 650B within the display image 511N or outside the display image 511N but within the high definition spatial image 700A. As mention previously, a centralization process may occur to select different pixels in the display image 511N from the high definition spatial image to position the fovea 650 more centrally in the display image 511N, such as illustrated by the image 702B in FIG. 7B which has a different matrix of pixels to display on the display 402L,402R. Within the display image 511N and/or within the high definition spatial image 700A, the fovea 650 is digitally moved from a first fovea position 650A displaying a first area of the surgical site to a second fovea position 650B displaying a second area of the surgical site.

Figure 7B:
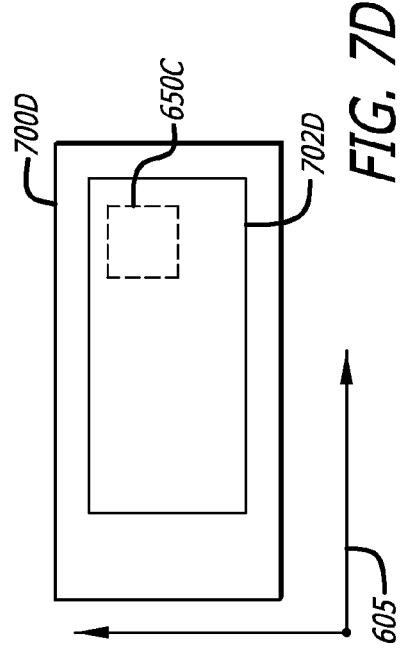

In FIG. 7B, the fovea position 650B is once again centered within the image 702B that is displayed on the display 402L, 402R. However, a surgeon or an assistant may desire to move the fovea 650 from the centered fovea position 650B in FIG. 7B to a different fovea position 650C outside of the display image 511N and the field of view of the surgical site captured by the high definition spatial image 700A corresponding to a given position of the endoscopic camera 101B. In this case, the endoscopic camera 101B may be mechanically panned to a different position to capture a different high definition spatial image to display pixels of the desired fovea position 650C.

The camera control system of the robotic surgical system may first move the fovea digitally. If the user out-paces the compensation rate of re-centering the fovea digitally, the camera control system transitions/ramps to full endoscopic camera drive for the motors of the robotic surgical arm 101B to mechanically move the endoscopic camera. This may happen as the as the user out-paces the compensation rate of the slow re-centering loop that is attempting to keep the zoomed region-of-interest centered in the video frame.

Note that moving an inner source window relative to an outer source window changes which pixels are mapped to the inner target window. If the source frame region between the inner and outer source windows is being mapped to a surround on the target display, then moving the inner source window may also change the warp of the pixels that are mapped to the surround. For example, in the surround the number of pixels may expand on one side while contracting on the opposite side.

As mentioned previously, the fovea 650 may be digitally moved from the first fovea position 650A to the second fovea position 650B within the display image 511N and/or within the high definition spatial image 700A. The fovea 650 may be digitally moved abruptly from the first fovea position 650A in one video frame to the second fovea position 650B in the next video frame. Alternatively, the fovea 650 may be digitally moved gradually from the first fovea position 650A to the second fovea position 650B over a sequence of video frames with intermediate fovea positions there-between.

Referring now to FIG. 8, the first fovea position 650A and the second fovea position 650B are illustrated with a plurality of intermediate fovea positions 850A-850D there-between. In this manner, the fovea 650 may appear to move more gradually from the first fovea position 650A to the second fovea position 650B within the display image 511N and/or within the high definition spatial image 700A.

Figure 7C:
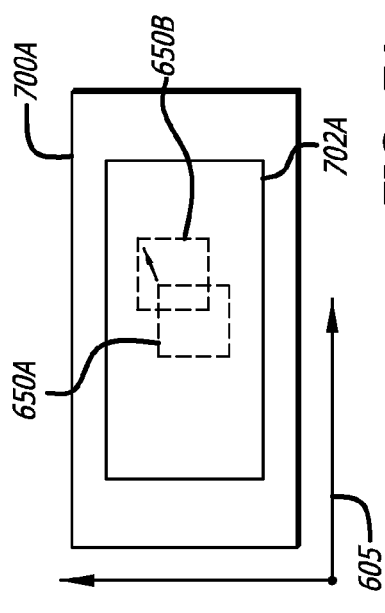

Referring now to FIG. 7C, not only may the display image 511N be digitally panned but the endoscopic camera 101B be mechanically panned. Additionally, a centering process that further adjust the digital panning of pixels and/or the mechanical panning of the endoscopic camera 101B may be used to adjust the display image 511N to an image position 702C around the fovea in order to center the desired fovea position 650C therein. In some cases, the centering process may be undesirable.

Figure 7D:
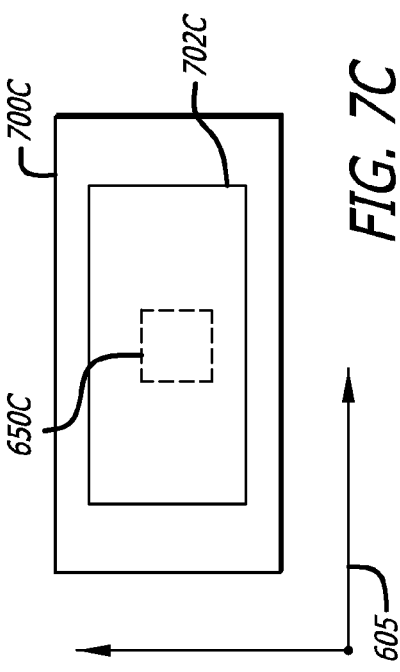

In FIG. 7D, the endoscopic camera 101B may be mechanically panned and the display image 511N may be digitally panned to a image position 702D but without any centering process so that the desired fovea position 650C is off-center within the display 402L,402R.

FIGS. 7C-7D illustrate combining digital image panning (digital tracking) with mechanical camera panning (servo-mechanical tracking). The digital image panning (digital tracking) can be combined with the mechanical camera panning (servo-mechanical tracking) analogous to a micro/macro mechanism or system. The digital image panning (digital tracking) makes the relatively small and faster deviations or tracking efforts—digital in this case. The mechanical camera panning (servo-mechanical tracking) can handle larger deviations that occur more slowly. Note that the effect of servo mechanical motion of the robotic surgical arm 101B and the endoscopic camera 101B may be compensated. The zoomed image or fovea 650 may be moved in the opposite direction of the movement of the endoscopic camera across the full special high definition image. In this case, the motion of the endoscopic camera 101B may be largely imperceptible when viewed in the zoomed image or fovea 650.

While automatic panning of the endoscopic camera 101B is possible, it may be preferable to avoid it and use digital panning alone. Otherwise, the endoscopic camera 101B may bump into something it should not unless precautions in its movement are taken. In this case, it is more desirable to digitally pan the fovea 650 from one position to another without requiring movement of the endoscopic camera.

Automatic Camera Following and Manual Selection of Image Position

In some embodiments of the invention, it may be desirable to have the image of the fovea or digital zoom area 650 automatically track or follow some direct or indirect motions of the surgeon without moving the endoscopic camera 101B. In other embodiments of the invention, it may be desirable to select the position of the fovea or digital zoom area 650 within the background image 651 of the display. In still other embodiments of the invention, it may be desirable combine characteristics of an automatic tracking system with a manual selection system such as by setting preferences or making a choice regarding the fovea or digital zoom area 650 and allow it to track a surgeon's motion in response thereto.

Automatic camera following and digital zoom are combined together such that the digital zoomed portion of an image tracks or follow a surgeon's motions, such as the gaze of his pupils, without requiring mechanical movement of the endoscopic camera. If the surgeon's motions indicate that the digital zoomed portion extend beyond pixels of the high definition digital image being captured, the endoscopic camera may be mechanically moved automatically.

For automatic camera following, different sensing modalities may be used to detect a surgeon's motion so that a digital zoomed portion of interest of an image may be moved around within the pixels of a high definition digital image. Some different sensing modalities include (1) robotic surgical tool tracking, (2) surgeon gaze tracking; (3) or a discrete user interface.

Robotic surgical tool tracking may be performed by kinematics sensing through joint encoders, potentiometers, and the like; video analysis-based tool location tracking; or a combination or fusion of kinematics sensing and video analysis-based tool location tracking. Robotic surgical tool tracking is further disclosed in U.S. patent application Ser. No. 11/130,471 entitled METHODS AND SYSTEM FOR PERFORMING 3-D TOOL TRACKING BY FUSION OF SENSOR AND/OR CAMERA DERIVED DATA DURING MINIMALLY INVASIVE ROBOTIC SURGERY filed by Brian David Hoffman et al. one May 16, 2005, which is incorporated herein by reference and in U.S. patent application Ser. No. 11/865,014 entitled METHODS AND SYSTEMS FOR ROBOTIC INSTRUMENT TOOL TRACKING filed by Wenyi Zhao et al. on Sep. 30, 2007, which is also incorporated herein by reference.

Figure 17A:
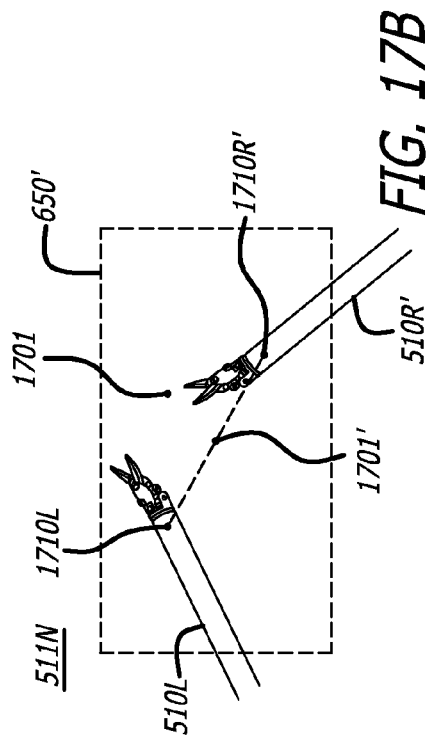
FIGS. 17A-17B illustrate a perspective view of an image and automatic panning of a fovea within the image using a tool centroid.
Figure 17B:
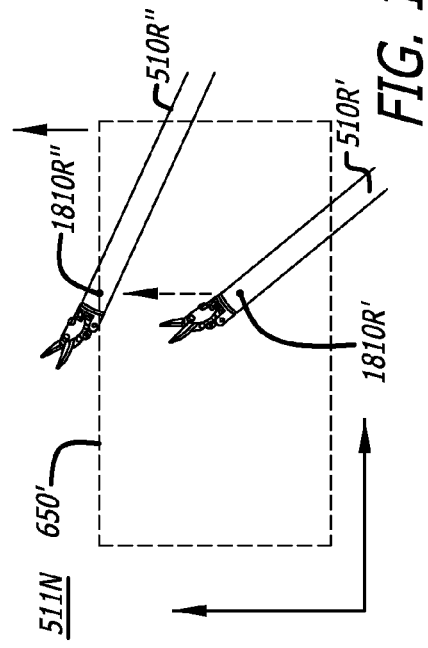

Referring now to FIGS. 17A-17B, a centroid (tool centroid) 1701 for the robotic surgical tools 510L,510R may be determined from the respective position information points 1710L,1710R within the surgical site determined from a tool tracking system. The tool centroid 1701 may be used as a center point to automatically position the center of the fovea 650 (re-center) within the image 511N.

For example, the robotic surgical tool 510R may shift in the surgical site to a position indicated by the robotic surgical tool 510R'. The position information follows the change in position of the tool to the respective position information point 1710R'. A new position of tool centroid 1701' is determined given the position information points 1710L,1710R'. This makes the fovea 650 off-center from the new position of the tool centroid 1701'. The new position of the tool centroid 1701' may be used as a center point to automatically re-center the fovea 650 within the image 511N.

FIG. 17B illustrates the fovea 650 re-centered within the image 511N in response to the new position of the tool centroid 1701'.

A discrete user interface may be provided to a surgeon at the master control console to control the position of the fovea 650 within the image 511N of the display. One or more buttons (such as arrow buttons to the side of a surgeon's console), one or more foot pedals, or the master control handles 160 themselves may be used to manipulate the position of the fovea 650 or other image. A voice recognition system at the master control console capable of recognizing vocal commands may also be used to adjust the position of the fovea 650.

One or more buttons, foot pedals, or combinations thereof may be pressed to manually move the fovea 650 or other images up, down, left, and/or right. Voice commands may be used in another configuration to move the fovea 650 or other images up, down, left, and/or right.

Alternatively, the discrete user interface may be used to actuate an automatic re-centering process of the digital zoomed image 650 based on current tool position, gaze location, or other available information in the surgical system. Alternatively, the discrete user interface may be used to re-center or move the image at discrete times, such as through voice activation, perhaps in concert with tool tracking or gaze detection.

As mentioned herein, the master control handles 160 themselves may be used to manipulate the position of the fovea 650 or other image. In such a case, one or both, of the master control handles 160 can serve as a two-dimensional or three-dimensional mouse (masters-as-mice). Accordingly, one or both of the master control handles 160 can be arranged to perform functions relative to the fovea image 650 in a manner analogous to a conventional mouse relative to a computer screen.

Each of the master control handles 160 may have at least six degrees of freedom of movement. Accordingly, when used as a three-dimensional mouse, a master control handle can be arranged to control six variables, for example. Therefore, functions such as, shifting, rotating, panning, tilting, scaling, and/or the like, can be performed simultaneously when one, or both, or either, of the masters are used as a three-dimensional mouse, without another input being required. In particular, for two-handed or two-master operation, any windows or overlays can be handled as "elastic" bodies, such that resizing, scaling, warping, and/or the like, can, for example, be controlled by pulling the masters apart, or the like.

One or both of the master control handles 160 may select and drag the fovea to different positions within the image 511N, either by adjusting its size/position within the image 511N, and/or by defining a crop rectangle to generate the fovea 650 from the background image 651 representative of the full spatial high definition images. The masters-as-mice functionality of the master control handles 160 can support successive refinement of the position of the fovea as well as control the level of image magnification or zoom within the high definition images.

In yet another configuration, the robotic surgical tools may be used to drag the fovea 650 to different positions within the image 511N and/or move the image 511N within the matrix of pixel information of the high definition images.

Figure 18A:
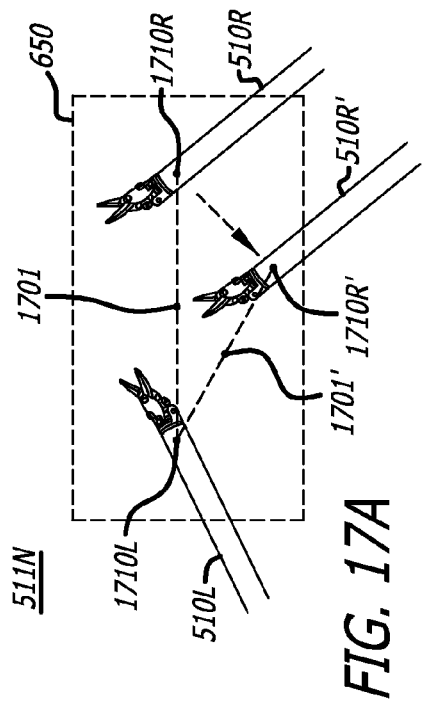
FIGS. 18A-18B illustrate a perspective view of an image and panning a fovea within the image using a robotic surgical tool to poke the fovea around therein.

Referring now to FIG. 18A, robotic surgical tool 510R has a position information point 1810 well away from the edge and closer to center of the fovea 650. A tool tracking system may be used to provide the information regarding the position information point 1810R of the robotic surgical tool relative to the endoscopic camera 101B. A surgeon may desire to move the fovea 650 within the image 511N to better magnify a different location within the surgical site. In this case, the robotic surgical tool 510 may act as a poker to poke or bump an edge of the fovea 650 to move up, down, left, right, and/or combinations thereof within the image 511N.

In an alternate embodiment of the invention with the fovea 650 in a fixed position in the center of the display, an elastic wall or other haptic interface may be simulated such that when the robotic surgical tool bumps into the outer edge of the fovea, or outer edge of the target window, the center position of the source area-of-interest pans accordingly to be within the fovea 650.

In FIG. 18A, the robotic surgical tool 510R has moved in position to robotic surgical tool position 510R' with the position information point 1810R' near the edge of the fovea 650. The digital zoom/panning system may pan the fovea 650 in response to the robot surgical tool being in the robotic surgical tool position 510R' with the position information point 1810R' substantially near the edge of the fovea 650.

Figure 18B:
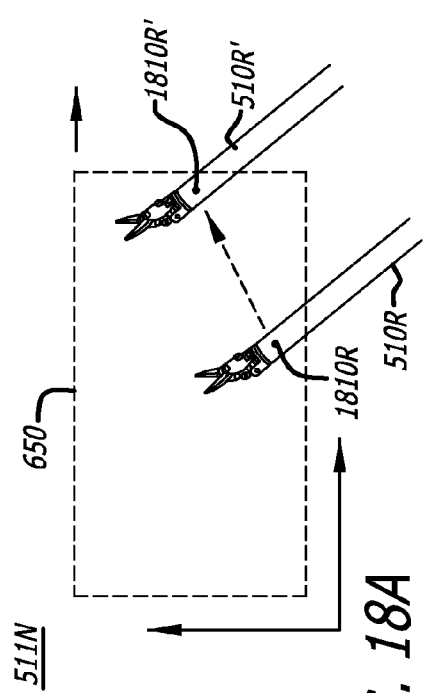

Referring now to FIG. 18B, the fovea 650 has panned from its position in FIG. 18A to the fovea position 650' so that the robotic surgical tool position 510R' and position information point 1810R' are more centered within the fovea. However, a surgeon may desire to move from the fovea position 650' to another position. In this case, the surgeon may use the robotic surgical tool again to pan the fovea 650. The robotic surgical tool 510R has moved in position from the robotic surgical tool position 510R' to the robotic surgical tool position 510R" with the position information point 1810R" near the top edge of the fovea 650. In this case, the fovea 650 will be panned up from its position 650" in FIG. 18B so that the robotic surgical tool position 510R" and position information point 1810R" will be more centered within the fovea.

One or more of the manual user interface techniques may be combined with an automatic user interface technique for digital panning/zooming.

Gaze Detection and Tracking

One of the sensing modalities that may be used for automatic camera following or image panning is gaze tracking of a surgeon's eyes in the stereo viewer 312.

As described with reference to FIGS. 4A-4C, the stereo viewer 312 may include one or more left gaze detection sensors 420L near the periphery of the display device 402L for the left eye of the surgeon and one or more right gaze detection sensors 420R near the periphery of the display device 402R for the right eye of the surgeon. One of the gaze detection sensors for each eye may also include a low level light source 422L,422R to shine light into the eye of the surgeon to detect eye movement with the respective gaze detection sensors 420L,420R.

The one or more left gaze detection sensors 420L and the one or more right gaze detection sensors 420R are used to determine the location of the central gaze of the surgeon's eyes within the image that is displayed on the display devices 402L,402R respectively. The central gaze location within the image may be used to define the center point of the fovea 650 within the image 511N. As the surgeon's gaze moves around with the image 511N, the fovea 650 may digitally move as well to provide a magnified image where the surgeon is gazing. Moreover, if the surgeon gazes in a location for a predetermined period of time, that area of the image may be digitally and/or mechanically automatically re-centered within the image 511N on the display devices 402L,402R. If instead the fovea 650 is in a fixed position in the center of the display, the surgeon's gaze off center of the image 511N for a predetermined period of time may shift the source area of interest to be in the center of the display within the fovea 650.

Exemplary algorithms for gaze detection and tracking are described in detail in "Gaze Contingent Control for Minimally Invasive Robotic Surgery" by Mylonas G. P., Darzi A, Yang G-Z. Computer Aided Surgery, September 2006; 11(5): 256-266; "Visual Search: Psychophysical Models and Practical Applications" by Yang G-Z, Dempere-Marco L, Hu X-P, Rowe A. Image and Vision Computing 2002; 20:291-305; and "Gaze Contingent Depth Recovery and Motion Stabilisation for Minimally Invasive Robotic Surgery" by George P. Mylonas, Ara Darzi, Guang-Zhong Yang; MIAR 2004, LNCS 3150, pp. 311-319, 2004. Exemplary algorithms for gaze detection and tracking are also described in U.S. Pat. No. 5,912,721 which is incorporated herein by reference.

The digitally formed fovea 650 and the digital panning of the fovea within the image 511N in response to gaze detection, allows the endoscopic camera 101B to remain stationary, at least for small adjustments. The automatic digital panning of the fovea 650 with the full spatial high definition image of the endoscopic camera in the background 651, a surgeon is less likely to be interrupted during surgery to change the view of images. That is, with the automatic digital panning of the fovea 650 and the full spatial high definition image in the background 651, a surgeon may avoid having to change the view of the surgical site by manual manipulation of the robotic arm 101B and the endoscopic camera. A decrease in surgeon interruption to change the view and manipulate the camera can improve the efficiency of the robotic surgical system.

Figure 9:
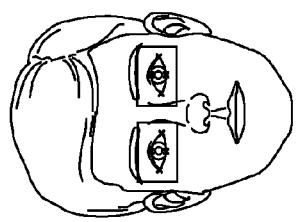
FIG. 9 illustrates a face with stereo gaze detection to detect left and right pupil positions.

Referring now to FIG. 9, a face is illustrated with stereo gaze detection about the left and right eyes to detect left and right pupil positions for gaze detection. The sensors may sense the pupil positions with respect to the left, right, top, and bottom edges of the eye. In FIG. 9, a surgeon may initially gaze directly ahead at a test pattern to calibrate the gaze detection system with left and right eyes gazing to a center position.

Figure 11B:
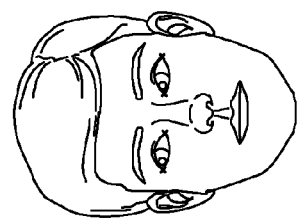
FIGS. 11A-11B illustrates a face with an upper left gaze position and a lower right left gaze position, respectively.
Figure 11A:
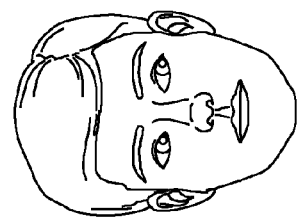

In contrast with the center position of FIG. 9, FIG. 11A illustrates left and right eyes gazing to an upper left position. FIG. 11B illustrates left and right eyes gazing to a lower right position.

Figure 10:
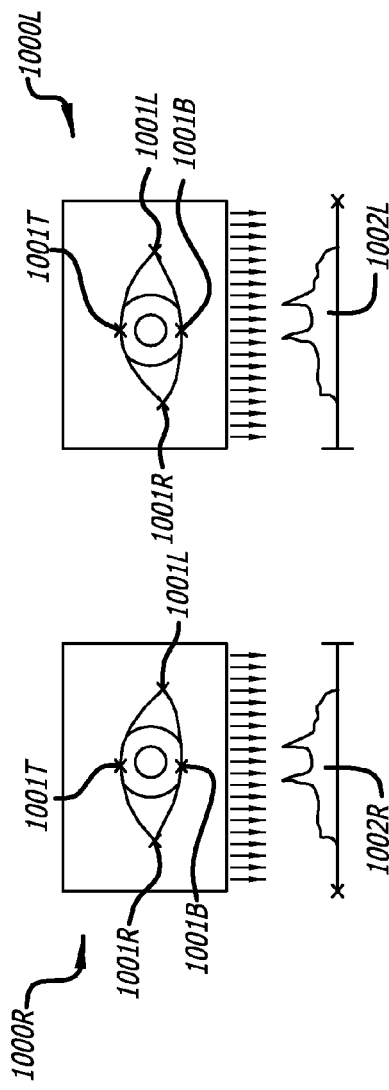
FIG. 10 illustrates left and rights graphs as to how the position of the pupil may be sensed with respect to the edges of the eye.

The gaze of the pupils can be detected in a number of different ways. FIG. 10 illustrates exemplary left and rights graphs 1002L, 1002R as to how the edges of the pupil may be sensed with respect to the top, bottom, left, and right corners 1001T, 1001B, 1001L, 1001R of the left and right eyes 1000R, 1000L.

The edge images for the right eye and left eye of may be formed via known methods, such as a Sobel filter or a Canny filter. The edge images can then be mapped in a direction perpendicular to the one-dimensional (1D) axis direction to detect the inner corners of the eyes. The image can then be scanned in a direction normal to the 1D-axis, with the lowest brightness point being the point of the inner corner of the eye. The peaks in the brightness points on the graphs 1002L, 1002R may indicate the position of the edges of the left and right pupils.

As the pupils move horizontally left or right, the position of the peaks along the graphs 1002R, 1002L shift respectively left or right. Similar graphs may be generated for vertical movement of the pupils up and down.

It may be desirable to detect head movement within the stereo viewer 312 for a more accurate gaze detection system. Head movement may be detected by one or more head motion sensors or algorithmically by using one or more gaze detection sensors 420L,420R. The level of head motion detected may be removed from gaze detection signals so that inadvertent head movement does not result in movement of the fovea 650 within the image 511N.

Figure 12:
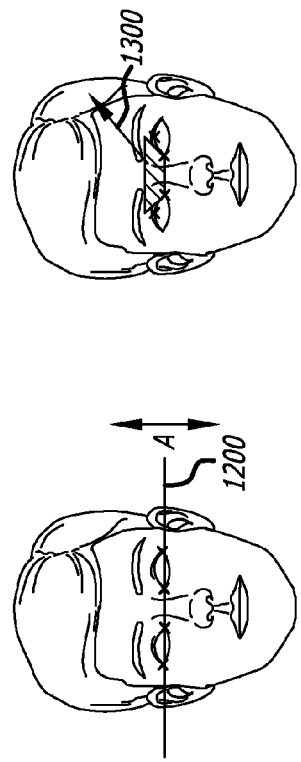
FIG. 12 illustrates how vertical head movement may be detected.

Referring now to FIG. 12, vertical head movement illustrated by arrow A may be detected by monitoring the movement of a line 1200 formed through the corners 1001L, 1001R of the left and right eyes. The corners of the left and right eyes may be determined from the edge images of the eyes.

Figure 13:
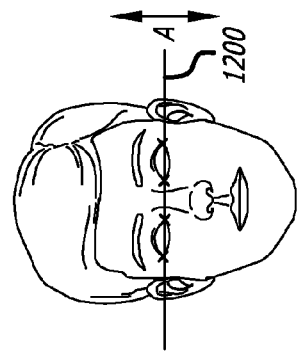
FIG. 13 illustrates how a combination of vertical and horizontal head movement may be detected.

Referring now to FIG. 13, a combination of vertical and horizontal head movement may be detected using at least two corners 1001T, 1001B, 1001L, 1001R of the left and right eyes. The top corner 1001T and the left corner 1000L of the right eye 1000R and the top corner 1001T and the right corner 1000R of the left eye 1000L may be used to form a polygon having a centroid. The centroid moves along a vector. The corners of the eyes may be monitored to detect movement in the centroid and the vector so that a combination of vertical and horizontal head movement may be detected.

Automatic Zoom Level

A surgeon may desire additional zoom or magnification of an object displayed in the fovea 650. Alternatively, the surgeon may desire less zoom or demagnification of an object displayed in the fovea 650. The level of the level of zoom may be set by manually by the selection of relative sizes of the source windows 661 and target windows 671 illustrated in FIG. 6D. However, methods of automatically determining an appropriate level of zoom may be made by automatically determining the relative sizes of the source windows 661 and target windows 671.

An approximation for the desired depth of the fovea 650 may be automatically determined by an average extent of instrument motion. The average extent may be determined by making a time weighted average of the motion in the robotic surgical instruments. Such extent defines a box or area within the image 511N or display 402L,402R. A determination of the minimum zoom that can display the box or area defined by the extent may be the appropriate level of zoom to select.

Gaze detection may also be used to automatically determine an approximation for the desired depth of the fovea 650. As the surgeons eyes move over the background 651 in the image 511N, the gaze motion of the surgeon's pupils or eyes may be stored over time. A time-weighted average of the stored gaze motion can be computed to automatically define a two dimensional area or a three dimensional surface within the image 511N or display 402L,402R. A determination of the minimum zoom that can display the two dimensional area or the three dimensional surface defined by the extent of the gaze motion of the surgeon's eyes may be the appropriate level of zoom to select.

In another configuration, the boundary defined by illumination falloff may be used to automatically select the source area of interest for display within the fovea 650.

If an automated digital panning occurs of the fovea 650 or the image under the fovea 650, the digital zoom may momentarily zoom out from the area of interest and then zoom back when the area of interest is substantially centered in the fovea 650.

A macro/micro approach can also be adapted along the insertion axis 574 (see FIG. 1C) of the endoscopic camera 101B mounted on the robotic surgical arm 158B. The endoscopic camera 101B may be physically and mechanically moved in and out of the surgical site along the insertion axis 574 by the motor 574 providing a macro adjustment. However initially from a fixed position, if the surgeon wishes to see a slightly narrower field of view, the camera can be virtually moved in along the insertion axis toward the tissue by increasing the digital zoom factor providing a micro adjustment, by decreasing the size of the area-of-interest selected from the source high definition video images. In this case, the endoscopic camera is virtually (electronically) moved by digital signal processing of the source video images without any physical or mechanical movement.

When the digital zoom exceeds a predetermined limit or the source window crosses over a predetermined lower size limit, the motor 574 may be engaged to physically and mechanically moved the endoscopic camera 101B along the insertion axis 574 to avoid an interpolation or a level of interpolation of the pixels (source pixels) in the source high definition video. This is analogous to mechanically moving (clutching) the camera along yaw/pitch axes when the fovea reaches the edge of the high definition video source. Alternately, endoscopic camera could be slowly adjusted along the insertion axis both electronically digitally and physically so as to maintain a source area-of-interest at a percentage (e.g., approximately 50%) of the source frame size. This is analogous to a slow slew/auto-recentering of the fovea.

The zoom factor for the fovea 650 may also be automatically determined by a distance from the end of the endoscopic camera to the operative site within the surgical cavity. This is analogous to auto-focus methods in digital cameras and how they derive an estimate of the working depth of focus.

Display Panel User Interface

Much of the discussion regarding digital zooming and digital panning is with regards to a surgeon O at the controls 160 of the master console 150. The same images seen by the surgeon in the stereo viewer may be monitored by an assistant on the external monitor 154 illustrated in FIGS. 1A-1B. However, the assistant A may also choose to see a different image than that of the surgeon without moving the endoscopic camera. The assistant A can control a second digital zoom and a second digital pan of the captured high definition digital images from the endoscopic camera 101B so that they can display a different view of images of the surgical site on a second display device, the external monitor 154. The assistant A may control the selection of the second digital zoom and the second digital pan on the monitor 154 in a number of ways.

Figure 14:
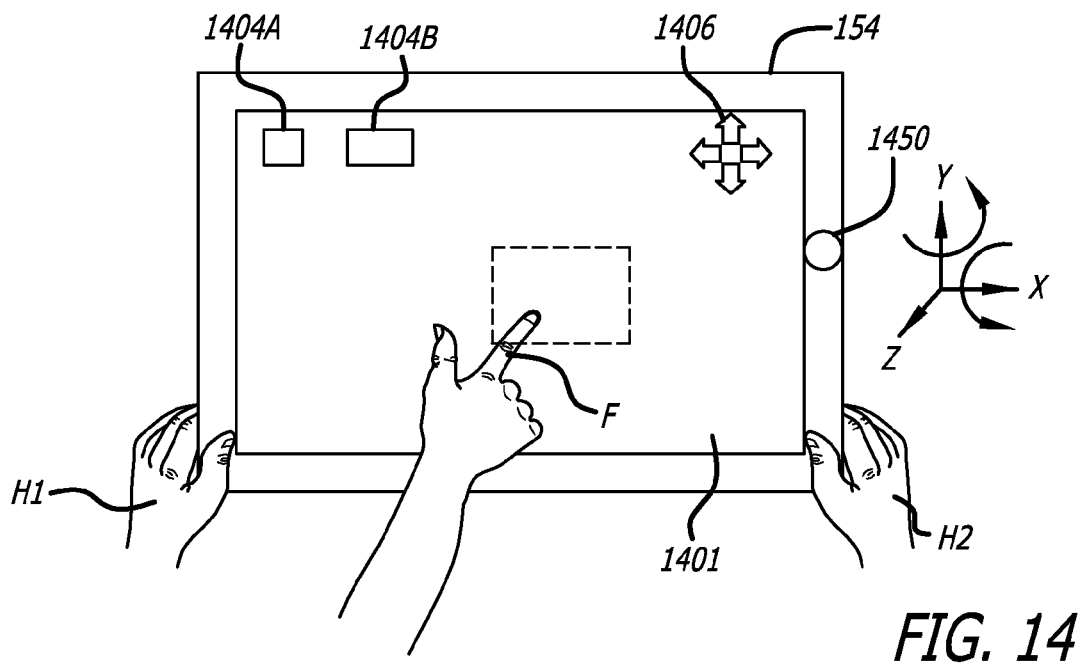
FIG. 14 illustrates a touch screen user interface in a display device to provide a control input to control a robotic surgical instrument such as an endoscopic camera.

Referring now to FIG. 14, the external monitor 154 may include a touch screen or touch panel interface 1401 to control the selection of the second digital zoom and the second digital pan on the monitor 154. For example, the assistant may touch his finger to the touch panel 1401 and select a region of the display to be the target window or fovea 650 with a linear digital zoom. With the fovea 650 defined and in a fixed position on the display, the assistant may then use one or more fingers F to scroll the image under the fovea to display a desired region of interest in the surgical site captured by the high definition source video images. Alternatively, a predetermined rectangular shape may be moved over the image on the touch panel with a finger F to select the desired region of interest to position within a fovea in the center of the display monitor 154. With the finger F on the touch panel 1401, the full frame image may be momentarily displayed on the touch panel 1401 so that the region of interest may be selected and then pop back out to zoomed-in view with the desired magnification of the fovea. In these cases, the assistant does not need to mechanically move the endoscopic camera 101B, avoiding clutching the robotic surgical arm 158B to physically move the endoscopic camera to another position.

Alternatively, one or more control buttons 1404A-1404B may be provided by the monitor 154 to digitally zoom and magnify the image provided by the fovea 650 or to digitally move the center of the fovea to another position within the surgical site. Up, down, left, and right pan arrows 1406 may be provided to pan the fovea within the captured pixels of the endoscopic camera to display a different fovea 650 within the image 511N.

In another configuration, the assistant may control the digital pan and the digital zoom for the fovea within the image by physical movement of the monitor 154. In this case, the monitor may include an inertia sensor 1450 to detect movement from an initial position 154A to various different positions such as positions 154B-154C illustrated in FIG. 15. For example, the inertia sensor 1450 may detect movement in the X and Y-axes to pan the fovea 650 around the image 511N displayed on the monitor 154. The inertia sensor 1450 may detect movement in the Z axis to zoom the fovea 650 in and out of the image 511N displayed on the monitor 154, for example.

Figure 15:
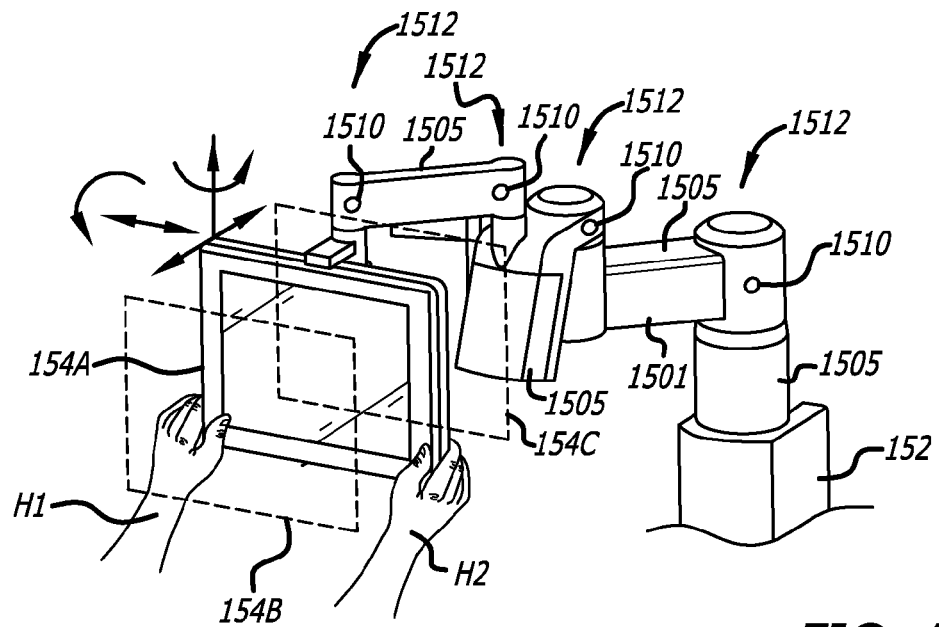
FIG. 15 illustrates manual movement of a display device to provide a control input to control a robotic surgical instrument such as an endoscopic camera.

Referring now to FIG. 15, a support arm 1501 includes a plurality of links 1505 to moveably support the monitor 154 coupled to the side cart 152. At a plurality of joints 1512 between the links 1505, the support arm includes a plurality of encoders 1510 in accordance with another embodiment of the invention.

In this case, the position of the monitor 154 is determined by the encoders 1510. The assistant may physically move the monitor 154 by grabbing it with their hands H1-H2. The movement in the monitor is translated to the joints through the links of the support arm 1501 and sensed by the encoders 1510. The encoders 1510 can detect movement from an initial position 154A to various different positions of the monitor 154 such as positions 154B-154C in order to digitally pan or digitally zoom the fovea 650. In this manner, intuitive camera control can be provided to the assistant, as an alternative to mechanically moving the camera with the camera clutch.

As another aspect of the invention, the monitor 154 may also be moved along and rotated about the axes to possibly control the movements of a robotic surgical tool 101, such as during initial set up or during surgery to control an extra tool, such as a suction tool for example. Another extra robotic surgical tool that may be controlled by an assistant is an ultrasound tool. The images generated by the ultrasound tool can be displayed on the monitor 154 as well the display devices 402L,402R in the stereo viewer 312. As the ultrasound tool is moved over surfaces in the surgical site, the ultrasound images that are displayed change.

System and Operational Methods

Figure 16:
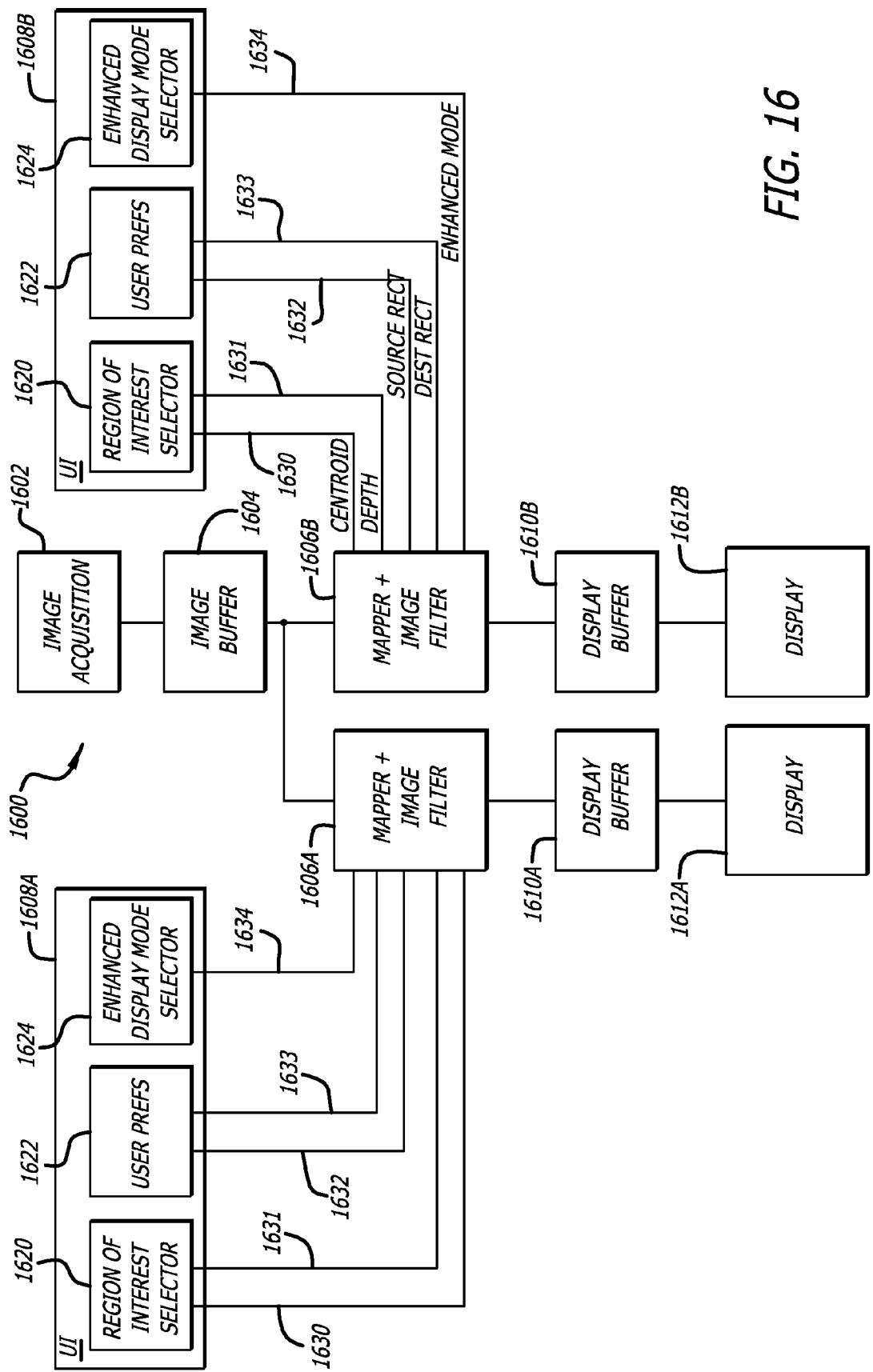
FIG. 16 is a functional block diagram of a digital video zoom subsystem to provide digital zoom portion and automatic panning of video information in a surgical site.

Referring now to FIG. 16, a functional block diagram of a digital video zoom subsystem 1600 is illustrated. The subsystem 1600 is an aspect of the robotic surgical system that may provide the digital zoom portion of video information and the automatic panning of video information in a surgical site.

The subsystem 1600 may include an image acquisition device (endoscopic camera) 1602, an image buffer 1604, a first digital mapper and image filter 1606A, a first user interface 1608A, a first display buffer 1610A, and a first display device 1612A coupled together as shown. The first display device 1612A may be one of the display device 154 or the stereo display devices 402L,402R, for example. The subsystem 1600 may further include a second digital mapper and image filter 1606B, a second user interface 1608B, a second display buffer 1610B, and a second display device 1612B coupled together as shown and independent of the first devices.

The image acquisition device 1602 may capture images of a surgical site in a high definition image format. The image buffer 1604 buffers one or more frames of a matrix of pixel data. The first digital mapper and image filter 1606 may map and filter the pixels in the captured images to properly display pixels on the first display device 1612A as desired. The first display buffer 1610 is coupled between the image filter 1606 and the first display device 1612A to store one or more frames of pixel information for display on the display device.

The first user interface 1608A may include a region of interest (fovea) selector 1620, a user preference selector 1622, and an enhanced display mode selector 1624 to select an enhanced display mode 1634. The region of interest (fovea) selector 1620 may function similar to the method and apparatus for automatic digital panning of the fovea 650 as described previously. A user may select how the source rectangle should automatically adjust its position with respect to an estimated tool centroid 1630, depth 1631, user focal-point, or mean working envelope, for example. The user preference selector 1622 allows a user to manually select the source data from a source rectangle 1632, such as a full-spatial high definition image, and manually select the destination rectangle 1633 for where the image may be preferably displayed on the first display device 1612A. Without the enhanced display mode being selected, the user may manually select the source rectangle 1632 and the destination rectangle 1633. If the system is selected to be in an enhanced display mode, the source rectangle 1632 and/or the destination rectangle 1633 may be automatically selected based on one or more of the estimated tool centroid 1630, the depth 1631, the user focal-point, or the mean working envelope. In some cases, a user may select a fixed destination rectangle while the source rectangle 1632 is automatically selected.

As the image acquisition device 1602 captures digital pixel data of images of a surgical site that are stored in the image buffer 1604, the pixel data can be independently selected for viewing by multiple display devices.

The second digital mapper and image filter 1606B, the second user interface 1608B, and the second display buffer 1610B are for independent selection and display of images on the second display device 1612B. For example, the first display 1612A may be the stereo display devices 402L,402R in the console 150 while the second display 1612B may be the assistant's display device 154 illustrated in FIG. 1A. A first user may independently select user preferences for the first display with the first user interface 1608A, while a second user may independently select user preferences for the second display with the second user interface 1608B. The second user interface 1608B is substantially similar to the first user interface 1608A and its description is incorporated herein by reference for brevity. Alternatively, the second digital mapper and image filter 1606B, the second user interface 1608B, and the second display buffer 1610B may be synchronized to the first devices such that the display of images on the second display device 1612B are similar to the display of images on the first display device 1612A.

Conclusion

The embodiments of the invention have now been described.

A number of elements of the system may be implemented in software and executed by a computer and its processor, such as computer 151 and its processor 302. When implemented in software, the elements of the embodiments of the invention are essentially the code segments to perform the necessary tasks. The program or code segments can be stored in a processor readable medium or transmitted by a computer data signal embodied in a carrier wave over a transmission medium or communication link. The processor readable medium may include any medium that can store or transfer information. Examples of the processor readable medium include an electronic circuit, a semiconductor memory device, a read only memory (ROM), a flash memory, an erasable programmable read only memory (EPROM), a floppy diskette, a CD-ROM, an optical disk, a hard disk, a fiber optic medium, a radio frequency (RF) link, etc. The computer data signal may include any signal that can propagate over a transmission medium such as electronic network channels, optical fibers, air, electromagnetic, RF links, etc. The code segments may be downloaded via computer networks such as the Internet, Intranet, etc.

While certain exemplary embodiments have been described and shown in the accompanying drawings, it is to be understood that such embodiments are merely illustrative of and not restrictive on the broad invention, and that the embodiments of the invention not be limited to the specific constructions and arrangements shown and described, since various other modifications may become apparent after reading the disclosure. For example, while the inner/outer pair of source windows 661 and inner/outer pair of target windows 671 have been shown and described as being rectangular in shape, they may be circular in shape in alternate embodiments of the invention. Additionally, some embodiments of the invention have been described with reference to a video system in a robotic surgical system. However, these embodiments may be equally applicable to other video systems. Thus, the embodiments of the invention should be construed according to the claims that follow below.

What is claimed is:

1. A method comprising:
capturing video images of a site, each image including an array of source pixels having pixel information of a first resolution;
selecting first inner and outer source windows in the video images for a first array of source pixels in the first inner source window and a first set of source pixels between the first inner and outer source windows;
selecting first inner and outer target windows in target pixels of a first display device for a first array of target pixels in the first inner target window and a first set of target pixels between the first inner and outer target windows;
mapping the first array of source pixels into the first array of target pixels;
mapping the first set of source pixels into the first set of target pixels; and
displaying on the first display device the first array of target pixels in the first inner target window and the first set of target pixels between the first inner and outer target windows around the first array of target pixels.

2. The method of claim 1, wherein
the mapping of the first array of source pixels into the first array of target pixels is a linear mapping; and
the mapping of the first set of source pixels into the first set of target pixels is a non-linear mapping.

3. The method of claim 2, wherein
the linear mapping is a linear scaling factor function,
the non-linear mapping is a bilinear interpolation function.

4. The method of claim 3, further comprising:
subdividing the first set of target pixels into a plurality of rectangular arrays of target pixels with four vertices of each being assigned a predetermined mapping from source pixels to target pixels, and
for the first set of target pixels in an interior of each of the plurality of rectangular arrays of target pixels, bilinearly interpolating between the first set of source pixels and the first set of target pixels.

5. The method of claim 2, further comprising:
adjusting the selection of the first inner source window to digitally zoom a first portion of the video images mapped into the first inner target window.

6. The method of claim 5, wherein
the size of the first inner source window is decreased to magnify the first portion of the video images mapped in the first inner target window.

7. The method of claim 5, wherein
the size of the first inner source window is increased to demagnify the first portion of the video images mapped in the first inner target window.

8. The method of claim 7, wherein
if the first inner source window becomes near the outer source window, the method further includes
adjusting a position of the first outer source window to center the first inner source window within the first outer source window.

9. The method of claim 8, further comprising
detecting motion of a user to automatically adjust the positions of the first inner and outer source windows.

10. The method of claim 9, wherein
the motion of the user to detect is one of a finger by a touch sensitive panel, a pair of hands by a motion sensing display device, a pair of eyes by a gaze detector, and a foot by a pedal.

11. The method of claim 2, further comprising:
adjusting a position of the first inner source window with respect to the first outer source window to digitally pan over source pixels in the video images.

12. The method of claim 2, wherein
the first inner and outer source windows are concentric, and the method further includes
adjusting positions of the first inner and outer source windows together to digitally pan over source pixels in the video images mapped into the first array of target pixels in the first inner target window and the first set of target pixels between the first inner and outer target windows.

13. The method of claim 2, wherein
the first inner and outer target windows are concentric, and the method further includes
adjusting positions of the first inner and outer target windows together to reposition the first inner and outer target windows in the first display.

14. The method of claim 2, further comprising:
adjusting a position of the first inner target window to digitally pan over target pixels in the first display device and reposition the first inner target window within the first outer target window.

15. The method of claim 1, wherein
the mapping of the first array of source pixels into the first array of target pixels is a first linear mapping; and
the mapping of the first set of source pixels into the first set of target pixels is a second linear mapping.

16. The method of claim 15, wherein
the first linear mapping is a linear scaling factor function, and
the second linear mapping is a piece-wise linear mapping.

17. The method of claim 1, further comprising:
selecting second inner and outer source windows in the video images for a second array of source pixels in the second inner source window and a second set of source pixels between the second inner and outer source windows;
selecting second inner and outer target windows in target pixels of a second display device for a second array of target pixels in the second inner target window and a second set of target pixels between the second inner and outer target windows;
mapping the second array of source pixels into the second array of target pixels;
mapping the second set of source pixels into the second set of target pixels; and
displaying on the second display device the second array of target pixels in the second inner target window and the second set of target pixels between the second inner and outer target windows around the second array of target pixels.

18. The method of claim 1, further comprising:
displaying on a second display device the first array of target pixels in the first inner target window and the first set of target pixels between the first inner and outer target windows around the first array of target pixels.

19. The method of claim 1, further comprising:
prior to displaying the first array of target pixels and the first set of target pixels, digitally filtering the first array of target pixels and the first set of target pixels.

20. The method of claim 1, wherein
the site is a minimally invasive surgical site and the video images are captured by a robotic endoscopic camera.

21. A method for a digital video system, the method comprising:
selecting an outer target window on a display device within which to display a fovea image and a surround image around the fovea image;
selecting an inner target window on the display device within the outer target window to display the fovea image;
linearly mapping source pixels of a digital video into target pixels in the inner target window to display the fovea image and non-linearly mapping source pixels of the digital video into target pixels between the inner target window and the outer target window to display the surround image around the fovea image.

22. The method of claim 21, wherein
the display device includes a touch sensitive display panel; and
the outer target window and the inner target window are selected by a touching a finger on the touch sensitive display panel.

23. The method of claim 22, further comprising:
touching the touch sensitive display panel with the finger to pan over the source pixels of the digital video for mapping into the inner target window of the display.

24. The method of claim 21, further comprising:
touching one or more buttons to pan over the source pixels of the digital video for mapping into the inner target window of the display.

25. The method of claim 21, further comprising:
adjusting the position of the display device to pan over the source pixels of the digital video for mapping into the inner target window of the display.

26. The method of claim 25, further comprising:
sensing the motion of the display device with an inertia sensor to digitally pan the source pixels of the digital video.

27. The method of claim 25, further comprising:
sensing the motion of the display device with one or more encoders at one or more joints of set-up arms supporting the display device.

* * * * *